(12) United States Patent
Khan et al.

(10) Patent No.: US 6,653,462 B2
(45) Date of Patent: Nov. 25, 2003

(54) NUCLEOTIDE COMPOUNDS INCLUDING A RIGID LINKER

(75) Inventors: Shaheer H. Khan, Foster City, CA (US); Barnett B. Rosenblum, San Jose, CA (US); Weiguo Zhen, Foster City, CA (US); Steven M. Menchen, Fremont, CA (US)

(73) Assignee: Applera Corporation, Foster City CA ( * ) Notice: Subject to any disclaimer, the term of this patent is extended or adjusted under 35 U.S.C. 154(b) by 0 days.

(21) Appl. No.: 10/085,561

(22) Filed: Feb. 26, 2002

(65) Prior Publication Data

US 2002/0151711 A1 Oct. 17, 2002

Related U.S. Application Data

(63) Continuation of application No. 09/461,506, filed on Dec. 14, 1999, which is a division of application No. 09/172,789, filed on Oct. 14, 1998, now Pat. No. 6,096,875, which is a continuation-in-part of application No. 09/087,250, filed on May 29, 1998, now Pat. No. 5,948,648.

(51) Int. Cl.[7] .................. C07H 21/00; C07H 21/02; C07H 21/04; C12Q 1/68
(52) U.S. Cl. .................. 536/23.1; 435/6; 536/22.1; 536/25.3; 536/25.32; 536/26.6
(58) Field of Search .............. 435/6; 536/23.1, 536/22.1, 25.3, 25.32, 26.6

(56) References Cited

U.S. PATENT DOCUMENTS 4,318,846 A    3/1982    Khanna et al.

(List continued on next page.)

FOREIGN PATENT DOCUMENTS

| EP | 0 710 667 A2 | 5/1996 |
|---|---|---|
| WO | WO98/20162 A3 | 5/1998 |
| WO | WO98/20162 A2 | 5/1998 |

OTHER PUBLICATIONS

Prober, J.M., et al., "A System for Rapid DNA Sequencing with Fluorescent Chain–Terminating Dideoxynucleotides," *Science*, US, American Association for the Advancement of Science, vol. 238, NR. 4825, pp. 336–341 (1987).

*Primary Examiner*—Jezia Riley
(74) *Attorney, Agent, or Firm*—Alex Andrus; Vincent P. Liptak; Paul D. Grossman

(57) ABSTRACT

A nucleoside/tide compound having the structure:

NUC-L-S-LB/LG is described wherein NUC is a nucleoside/tide having a nucleobase portion B, L is a rigid linkage, S is a spacer; and LB/LG is a member of a linkage pair or a label. NUC is attached to L through B such that when B is a purine, L is attached to the 8-position of the purine, when B is 7-deazapurine, L is attached to the 7-position of the 7-deazapurine, and when B is pyrimidine, L is attached to the 5-position of the pyrimidine. In an important aspect of the invention, L has the structure:

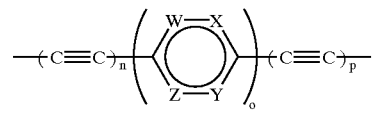

wherein each of n, o and p are integers ranging from 0 to 3, and the sum of n, o and p is at least 2, and each of W, X, Y and Z is selected from the group consisting of carbon and nitrogen. The invention further includes polynucleotide compounds comprising the nucleoside/tide, and primer extension methods utilizing the nucleoside/tide, particularly when used in combination with certain mutant polymerase enzymes.

37 Claims, 19 Drawing Sheets

U.S. PATENT DOCUMENTS

| | | |
|---|---|---|
| 5,047,519 A | 9/1991 | Hobbs, Jr. et al. |
| 5,151,507 A | 9/1992 | Hobbs, Jr. et al. |
| 5,171,534 A | 12/1992 | Smith et al. |
| 5,188,934 A | 2/1993 | Menchen et al. |
| 5,366,860 A | 11/1994 | Bergot et al. |
| 5,770,716 A | 6/1998 | Khan et al. |
| 5,844,106 A | 12/1998 | Seela et al. |
| 5,948,648 A | 9/1999 | Khan et al. |
| 6,096,273 A | 8/2000 | Kayyem et al. |
| 6,096,875 A | 8/2000 | Khan et al. |
| 6,150,510 A | 11/2000 | Seela et al. |
| 6,197,555 B1 | 3/2001 | Khan et al. |
| 6,221,583 B1 | 4/2001 | Kayyem et al. |
| 6,232,062 B1 | 5/2001 | Kayyem et al. |

NUCLEOTIDE COMPOUNDS INCLUDING A RIGID LINKER

This non-provisional application is a continuation of application Ser. No. 09/461,506 filed Dec. 14, 1999, now pending, which is a divisional of application Ser. No. 09/172,789 filed Oct. 14, 1998, now U.S. Pat. No. 6,096,875, issued Aug. 1, 2000, which is a continuation-in-part of Ser. No. 09/087,250 filed May 29, 1998, now U.S. Pat. No. 5,948,648, all of which are incorporated herein by reference.

FIELD OF THE INVENTION

This invention relates generally to nucleosite/tide compounds useful as substrates for polymerase enzymes, methods for using such compounds in a primer extension reaction, and polynucleotides containing such nucleotide compounds.

BACKGROUND

Nucleic acid sequencing has become a vitally important technique in modem biology and biotechnology, providing information relevant to fields ranging from basic biological research to drug discovery to clinical medicine. Because of the large volume of DNA sequence data to be collected, automated techniques have been developed to increase the throughput and decrease the cost of nucleic acid sequencing methods, e.g., U.S. Pat. No. 5,171,534; Connell et al., *Biotechniques*, 5(4): 342–348 (1987); and Trainor, *Anal. Chem.*, 62: 418–426 (1990).

A preferred automated nucleic acid sequencing method is based on the enzymatic replication technique developed by Sanger, et al., *Proc. Natl. Acad. Sci.*, 74: 5463–5467 (1977). In Sanger's technique, the sequence of a single-stranded template nucleic acid is determined using a nucleic acid polymerase to synthesize a set of polynucleotide fragments wherein the fragments (i) have a sequence complementary to the nucleic acid sequence, (ii) differ in length by a single nucleotide, and (iii) have a 5'-end terminating in a known nucleotide, e.g., A, C, G, or T. In the method, an oligonucleotide primer is hybridized to a 3'-end of the template nucleic acid to be sequenced, the 3'-end of the primer serving as an initiation site for polymerase-mediated polymerization of a complementary polynucleotide fragment. The enzymatic polymerization step, or primer extension reaction, is carried out by combining the template-primer hybrid with the four extendible nucleotides, e.g., deoxynucleotides ("dNTPs"), a nucleic acid polymerase enzyme, and a nucleotide "terminator", e.g., 2',3'-dideoxynucleotide triphosphate ("ddNTP"). The incorporation of the terminator forms a primer extension product which lacks a hydroxy group at the 3'-terminus and thus can not be further extended by the polymerase, i.e., the extension product is "terminated". The competition between the ddNTP and its corresponding terminator for incorporation results in a distribution of different-sized extension products, each extension product terminating with the particular terminator used in the reaction. To discover the complete sequence of the template nucleic acid, four parallel reactions are run, each reaction using a different terminator. To determine the size distribution of the extension products, the extension products are separated by electrophoresis such that products differing in size by a single nucleotide are resolved.

In a modern variant of the classical Sanger technique, each nucleotide terminator is labeled with a fluorescent dye, e.g., Prober et al., *Science*, 238: 336–341 (1987); and U.S. Pat. No. 5,151,507, and a thermostable DNA polymerase enzyme is used, e.g., Murray, *Nucleic Acids Research*, 17(21): 8889 (1989). Several advantages are realized by utilizing dye-labeled terminators, e.g., (i) problems associated with the storage, use and disposal of radioactive isotopes are eliminated, (ii) the requirement to synthesize dye-labeled primers is eliminated, and, (iii) when using a different dye label for each A, G, C, or T terminator, all four primer extension reactions can be performed simultaneously in a single tube. Using a thermostable polymerase enzyme provides several additional advantages, e.g., (i) the polymerization reaction can be run at elevated temperature thereby disrupting any secondary structure of the template, resulting in fewer sequence-dependent artifacts, and (ii) the sequencing reaction can be thermocycled, thereby serving to linearly amplify the amount of extension product produced, thus reducing the amount of template nucleic acid required to obtain a reliable sequence.

While these modern variants on Sanger sequencing methods have proven effective, several problems remain with respect to optimizing their performance and economy. One problem encountered when using presently available dye-labeled terminators in combination with thermostable polymerase enzymes in a Sanger-type nucleic acid sequencing process, particularly in the case of fluorescein-type dye labels, is that a large excess of dye-labeled terminator over the unlabeled extendible nucleotides is required, e.g., up to a ratio of 50:1. This large excess of labeled terminator makes it necessary to purify the sequencing reaction products prior to performing the electrophoretic separation step in order to avoid interference caused by the comigration of unincorporated labeled terminator species and bona fide labeled sequencing fragments. A typical clean-up method includes an ethanol precipitation or a chromatographic separation as described in *ABI PRISM™ Dye Terminator Cycle Sequencing Core Kit Protocol*, PE Applied Biosystems, Revision A, p/n 402116 (August 1995). Such a clean-up step greatly complicates the task of developing totally automated sequencing systems wherein the sequencing reaction products are transferred directly into an electrophoretic separation process.

A second problem encountered when using presently available dye-labeled terminators in combination with a thermostable polymerase in a Sanger-type nucleic acid sequencing process is that the extent of incorporation of labeled terminators into a primer extension product is variable and therefore results in an uneven distribution of peak heights when the primer extension products are separated by electrophoresis and detected using fluorescence detection. Such uneven peak heights are disadvantageous because they make automated sequence determination and heterozygote detection substantially less reliable.

Thus, there remains a continuing need for labeled nucleotide terminator compounds which do not require a large excess over unlabeled extendable nucleotides in a primer extension reaction and, which produce an even peak height distribution in a Sanger-type sequencing reaction.

SUMMARY

The present invention is directed towards our discovery of a novel class of nucleoside/tide compounds including a rigid linker portion and methods for using such compounds. These compounds are particularly useful as labeled terminators and as labeled chain-extending nucleotides in a primer extension reaction, e.g., in a Sanger-type DNA sequencing reaction or in a PCR reaction.

It is an object of the invention to provide a nucleotide which can be used to form a labeled chain-terminating or chain-extending nucleotide.

It is a further object of the invention to provide a labeled chain-terminating or chain-extending nucleotide.

It is yet an additional object of the invention to provide a chain-terminating nucleotide which includes a fluorescent label wherein a reduced excess concentration of such labeled chain-terminating nucleotide over an unlabeled chain-terminating nucleotide is required in a Sanger-type DNA sequencing process.

It is another object of the invention to provide a labeled chain-terminating nucleotide which results in a more even distribution of peak heights in a Sanger-type DNA sequencing process.

It is another object of the invention to provide labeled polynucleotides.

It is an additional object of the invention to provide methods including a primer extension reaction utilizing the nucleotide compounds of the invention.

In a first aspect, the foregoing and other objects of the invention are achieved by a nucleoside/tide compound having the structure

NUC-L-S-LB/LG wherein NUC is a nucleoside/tide having a nucleobase portion B, L is a rigid linkage, S is a spacer, and LB/LG is a member of a linkage pair or a label. NUC is attached to L through B such that when B is a purine, L is attached to the 8-position of the purine, when B is 7-deazapurine, L is attached to the 7-position of the 7-deazapurine, and when B is pyrimidine, L is attached to the 5-position of the pyrimidine. In an important feature of the present invention, L has the structure

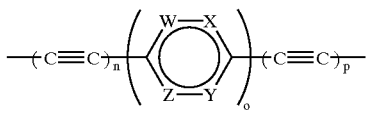

wherein each of n, o and p are integers ranging from 0 to 3, and the sum of n, o and p is at least 2, and each of W, X, Y and Z is either carbon or nitrogen.

In a second aspect, the present invention includes polynucleotides incorporating the above-described nucleoside/tide compounds.

In a third aspect, the present invention includes a method for performing a primer extension reaction comprising the steps of providing a template nucleic acid, annealing an oligonucleotide primer to a portion of the template nucleic acid for forming a primer-template hybrid, and adding primer-extension reagents to the primer-template hybrid for extending the primer, where the primer extension reagent includes a nucleoside/tide compound as described above.

These and other objects, features, and advantages of the present invention will become better understood with reference to the following description, drawings, and appended claims.

DETAILED DESCRIPTION OF THE PREFERRED EMBODIMENTS

Figure 1:
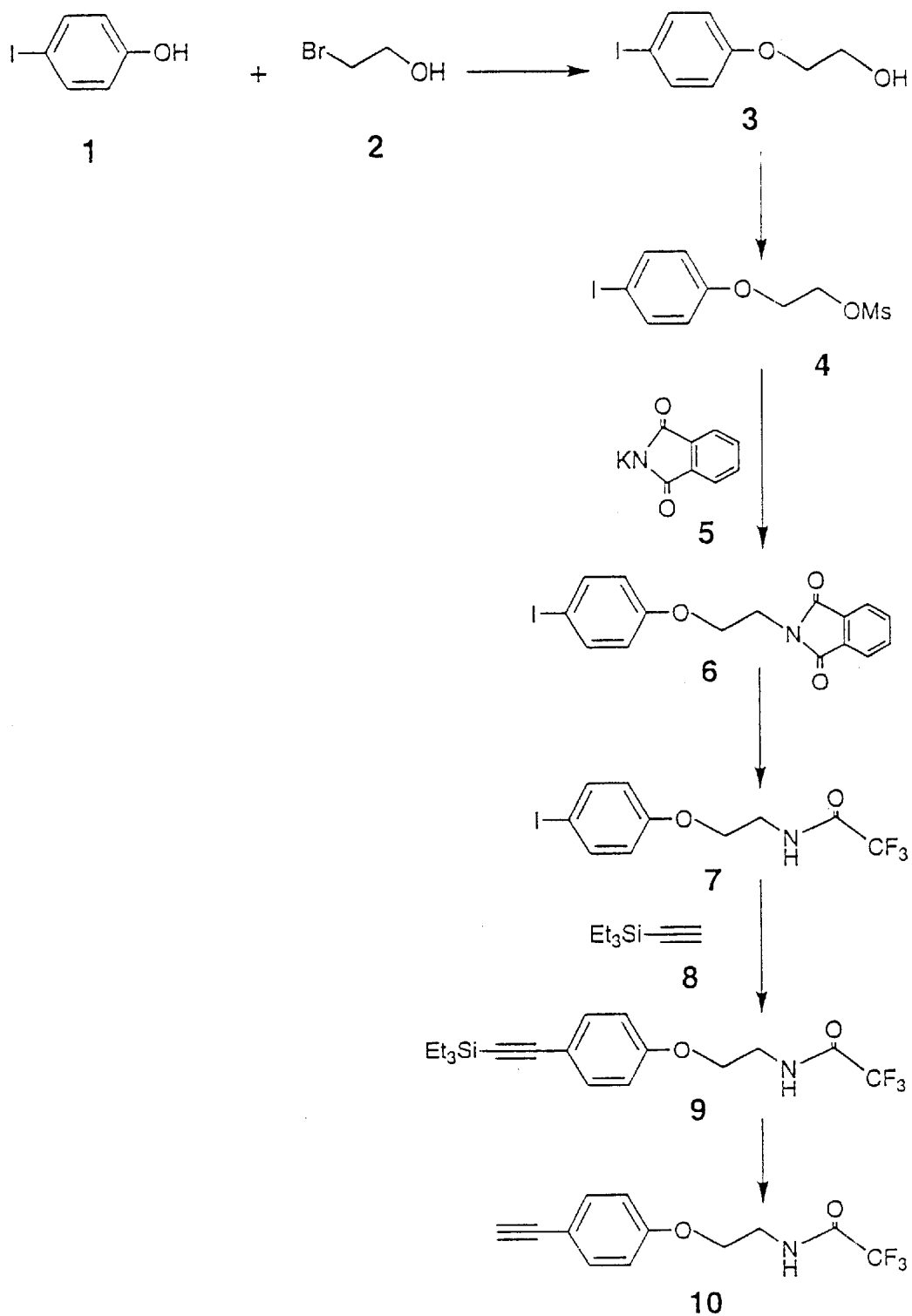
FIG. 1 shows the synthesis of compound 10 of the present invention.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Generally, the present invention comprises a novel class of nucleoside/tide compounds useful as substrates for polymerase enzymes, polynucleotides including such compounds, and methods for using such compounds in a primer extension reaction. The compounds of the present invention find particular application in the preparation of dye labeled nucleotide chain-terminating agents for use in Sanger-type DNA sequencing methods, and, in the preparation of dye labeled nucleotide chain-extending agents for use in methods including a primer extension reaction, e.g., PCR.

The invention is based in part on the discovery that the subject nucleotides are particularly good substrates for thermostable DNA polymerase enzymes, i.e., (i) a significantly reduced molar excess is required in a Sanger-type DNA sequencing reaction relative to that required when using currently available labeled terminators, and, (ii) a more even distribution of peak heights is seen in a Sanger-type DNA sequencing process relative to that seen when using currently available labeled terminators.

I. Definitions

Unless stated otherwise, the following terms and phrases as used herein are intended to have the following meanings:

"Taq polymerase" means a DNA polymerase enzyme from the organism *Thermus aquaticus*, including mutant and/or recombinant forms thereof.

The term "label" refers to a moiety that, when attached to the nucleoside/tides of the invention, render such nucleoside/tides, and polynucleotides containing such nucleotides, detectable using known detection means. Exemplary labels include fluorophores, chromophores, radioisotopes, spin-labels, enzyme labels, chemiluminescent labels, and the like, which allow direct detection of a labeled compound by a suitable detector, or, a ligand, such as an antigen, or biotin, which can bind specifically with high affinity to a detectable anti-ligand, such as a labeled antibody or avidin. Preferably the labels are fluorescent dyes such as fluorescein-type or rhodamine-type dyes.

"Linking group" means a moiety capable of reacting with a "complementary functionality" to form a "linkage." A linking group and its associated complementary functionality is referred to herein as a "linkage pair." Preferred linkage pairs include a first member selected from the group isothiocyanate, sulfonyl chloride, 4,6-dichlorotriazinyl, succinimidyl ester, or other active carboxylate, and a second member that is amine. Preferably a first member of a linkage pair is maleimide, halo acetyl, or iodoacetamide whenever the second member of the linkage pair is sulfhydryl. See R. Haugland, *Molecular Probes Handbook of Fluorescent Probes and Research Chemicals*, Molecular probes, Inc. (1992). In a particularly preferred embodiment, the first member of a linkage pair is N-hydroxysuccinimidyl (NHS) ester and the second member of the linkage pair is amine, where, to form the NHS ester, a carboxylate moiety is reacted with dicyclohexylcarbodiimide and N-hydroxysuccinimide.

The term "nucleoside" refers to a compound consisting of a purine, deazapurine, or pyrimidine nucleobase, e.g., adenine, guanine, cytosine, uracil, thymine, deazaadenine, deazaguanosine, and the like, linked to a pentose at the 1'-position. When the nucleoside base is purine or 7-deazapurine, the pentose is attached to the nucleobase at the 9-position of the purine or deazapurine, and when the nucleobase is pyrimidine, the pentose is attached to the nucleobase at the 1-position of the pyrimidine, e.g., Kornberg and Baker, *DNA Replication,* 2nd Ed. (Freeman, San Francisco, 1992). The term "nucleotide" as used herein refers to a phosphate ester of a nucleoside, e.g., a triphosphate ester, wherein the most common site of esterification is the hydroxyl group attached to the C-5 position of the pentose. The term "nucleoside/tide" as used herein refers to a set of compounds including both nucleosides and nucleotides. "Analogs" in reference to nucleosides/tides include synthetic analogs having modified nucleobase portions, modified pentose portions and/or modified phosphate portions, e.g. described generally by Scheit, *Nucleotide Analogs* (John Wiley, New York, 1980). Generally, phosphate analogs comprise analogs of phosphate wherein the phosphorous atom is in the +5 oxidation state and one or more of the oxygen atoms is replaced with a non-oxygen to moiety, e.g., sulfur. Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present. Exemplary base analogs include but are not limited to 2,6-diaminopurine, hypoxanthine, pseudouridine, C-5-propyne, isocytosine, isoguanine, 2-thiopyrimidine, and other like analogs. Exemplary sugar analogs include but are not limited to 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro and bromo. The term "labeled nucleoside/tide" refers to nucleosides/tides which are covalently attached to the dye compounds of Formula I through a linkage.

The terms "polynucleotide" or "oligonucleotide" mean polymers of nucleotide monomers or analogs thereof, including double and single stranded deoxyribonucleotides, ribonucleotides, α-anomeric forms thereof, and the like. Usually the monomers are linked by phosphodiester linkages, where as used herein, the term "phosphodiester linkage" refers to phosphodiester bonds or bonds including phosphate analogs thereof, including associated counterions, e.g., $H^+$, $NH_4^+$, $Na^+$, if such counterions are present. Polynucleotides typically range in size from a few monomeric units, e.g. 5–40, to several thousands of monomeric units. Whenever a polynucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes deoxythymidine, unless otherwise noted.

The term "substituted" means a molecule wherein one or more hydrogen atoms are replaced with one or more non-hydrogen atoms, functional groups or moieties. For example, an unsubstituted nitrogen is —$NH_2$, while a substituted nitrogen is —$NHCH_3$, and an unsubstituted carbon is —$CH_3$, while a substituted carbon is —$CH_2Cl$. Exemplary substituents include but are not limited to halo, e.g., fluorine and chlorine, lower alkyl, lower alkene, lower alkyne, sulfate, sulfonate, sulfone, amino, ammonium, amido, nitrile, lower alkoxy, phenoxy, aromatic, phenyl, polycyclic aromatic, electron-rich heterocycle water-solubilizing group, and linking group.

"Polycyclic aromatic" means aromatic hydrocarbons having multiple ring structures including biaryls and condensed benzenoid hydrocarbons. The biaryls are benzenoid compounds where two or more rings are linked together by a single bond. The parent system of this class is biphenyl. The condensed benzenoid compounds are characterized by two or more benzene rings fused together at ortho positions in such a way that each pair of rings shares two carbons. The simplest members of this group are napthalene, with two rings, and anthracene and phenanthrene, each with three rings.

"Electron-rich heterocycle" means cyclic compounds in which one or more ring atoms are not carbon, i.e., are hetero atoms, and the heteroatoms have unpaired electrons which contribute to a 6-π electronic system. Exemplary electron-rich heterocycles include but are not limited to pyrrole, indole, furan, benzofuran, thiophene, benzothiophene and other like structures.

"Linking group" means a moiety capable of reacting with a "complementary functionality" attached to a reagent or member of an energy transfer dye pair, such reaction forming a "linkage" connecting the dye to the reagent or member of the energy transfer dye pair. Preferred linking groups include isothiocyanate, sulfonyl chloride, 4,6-dichlorotriazinyl, succinimidyl ester, or other active carboxylate whenever the complementary functionality is amine. Preferably the linking group is maleimide, halo acetyl, or iodoacetamide whenever the complementary functionality is sulfhydryl. See R. Haugland, *Molecular Probes Handbook of Fluorescent Probes and Research Chemicals*, Molecular probes, Inc. (1992). In a particularly preferred embodiment, the linking group is a N-hydroxysuccinimidyl (NHS) ester and the complementary functionality is an amine, where to form the NHS ester, a dye of the invention including a carboxylate linking group is reacted with dicyclohexylcarbodiimide and N-hydroxysuccinimide.

"Water solubilizing group" means a substituent which increases the solubility of the compounds of the invention in aqueous solution. Exemplary water-solubilizing groups include but are not limited to quaternary amine, sulfate, sulfonate, carboxylate, phosphate, polyether, polyhydroxyl, and boronate.

The term "xanthene-type dye" refers to a class of dye molecules which include the following fused three-ring system:

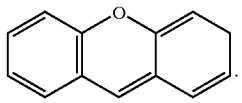

The term "fluorescein-type dye" refers to a class of xanthene dye molecules which include the following substituted fused three-ring system:

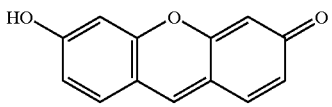

where a wide variety of substitutions are possible at each deoxy ring position. A particularly preferred subset of fluorescein-type dyes include the 4,7,-dichorofluoresceins (Menchen). Examples of fluorescein-type dyes used as fluorescent labels in DNA sequencing methods include 6-carboxyfluorescein (6-FAM), 5-carboxyfluorescein (5-FAM), 5 or 6-carboxy-4,7,2',7'-tetrachlorofluorescein (TET), 5 or 6-carboxy-4,7,2',4',5',7'-hexachlorofluorescein (HEX), 5-or 6-carboxy-4',5'-dichloro-2'7'-dimethoxyfluorescein (JOE), and 5-carboxy-2',4',5',7'-tetrachlorofluorescein (ZOE). Many times the designation −1 or −2 is placed after an abbreviation of a particular dye, e.g., HEX-1. The "−1" and "−2" designations indicate the particular 5 or 6 dye isomer being used. The 1 and 2 isomers are defined by the elution order (the 1 isomer being the first to elute) of free dye in a reverse-phase chromatographic separation system utilizing a C-8 column and an elution gradient of 15% acetonitrile/85% 0.1 M triethylammonium acetate to 35% acetonitrile/65% 0.1 M triethylammonium acetate.

The term "rhodamine-type dye" refers to a class of xanthene dye molecules which include the following fused three-ring system:

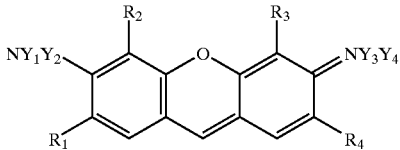

where preferably $Y_1$–$Y_4$ taken separately are hydrogen or lower alkyl, or, when taken together, $Y_1$ and $R_2$ is propano and $Y_2$ and $R_1$ is propano, or, when taken together, $Y_3$ and $R_3$ is propano and $Y_4$ and $R_4$ is propano. A wide variety of substitutions are possible at each deoxy ring position including the $R_1$–$R_4$ positions. Exemplary rhodamine type dyes useful as nucleoside/tide labels include tetramethylrhodamine (TAMRA) 4,7-diclorotetramethyl rhodamine (DTAMRA), rhodamine X(ROX), rhodamine 6G(R6G), rhodamine 110 (R110), and the like (Bergot, et al., U.S. Pat. No. 5,366,860 (1994); Lee et al, *Nucleic Acids Research*, 20(10): 2471–2483 (1992)).

As used herein the term "primer-extension reagent" means a reagent including components necessary to effect the enzymatic template-mediated extension of an oligonucleotide primer. Primer extension reagents include: (i) a polymerase enzyme, e.g., a thermostable polymerase enzyme such as Taq polymerase; (ii) a buffer; (iii) chain-extension nucleotides, e.g., deoxynucleotide triphosphates, e.g., deoxyguanosine 5'-triphosphate, 7-deazadeoxyguanosine 5'-triphosphate, deoxyadenosine 5'-triphosphate, deoxythymidine 5'-triphosphate, deoxycytidine 5'-triphosphate; and, optionally in the case of Sanger-type DNA sequencing reactions, (iv) one or more chain-terminating nucleotides, e.g., dideoxynucleotide triphosphates, e.g., dideoxyguanosine 5'-triphosphate, 7-deazadideoxyguanosine 5'-triphosphate, dideoxyadenosine 5'-triphosphate, dideoxythymidine 5'-triphosphate, and dideoxycytidine 5'-triphosphate.

"Template nucleic acid" refers to any nucleic acid which can be presented in a single stranded form and is capable of annealing with a primer oligonucleotide. Exemplary template nucleic acids include DNA, RNA, which DNA or RNA may be single stranded or double stranded. More particularly, template nucleic acid may be genomic DNA, messenger RNA, cDNA, DNA amplification products from a PCR reaction, and the like. Methods for preparation of template DNA may be found elsewhere, e.g., *ABI PRISM™ Dye Primer Cycle Sequencing Core Kit with AmpliTaq® DNA Polymerase, FS, Protocol*, Revision C, p/n 402114 (1996).

II. Nucleotide Compounds

A. Structure

In a first aspect, the present invention comprises a novel class of nucleoside/tide compounds including a rigid linker useful as a polymerase substrate, e.g., in a Sanger-type DNA sequencing reaction. These compounds have the general structure shown in Formula I immediately below, including substituted forms thereof,

NUC-L-S-LB/LG         FORMULA I wherein NUC is a nucleoside/tide having a nucleobase portion B, L is a rigid linkage, S is a spacer, and LB/LG is a linking group or a label. NUC is attached to L through B such that when B is a purine, L is attached to the 8-position of the purine, when B is 7-deazapurine, L is attached to the 7-position of the 7-deazapurine, and when B is pyrimidine, L is attached to the 5-position of the pyrimidine. In an important feature of the compounds of the invention, L has the structure:

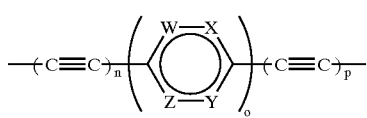

wherein each of n, o and p are integers ranging from 0 to 3, the sum of n, o and p is at least 2, and each of W, X, Y and Z is selected from the group consisting of —CH and nitrogen, including substituted forms thereof.

NUC can be any suitable nucleoside, nucleotide, or analog thereof. However, in a preferred embodiment, a sugar-portion of NUC is selected from the group consisting of 2'-deoxyribonucleotide, 3'-deoxyribonucleotide, 2',3'-dideoxyribonucleotide, 2',3'-dideoxy-3'-fluoro-ribonucleotide, 2',3'-dideoxy-2'-fluoro-ribonucleotide, 2',3'-dideoxy-3'-azido-ribonucleotide, 2',3'-dideoxy-2'-azido-ribonucleotide, 2',3'-dideoxy-2'-amino-ribonucleotide, 2',3'-dideoxy-3'-amino-ribonucleotide, and 2',3'-dehydroribonucleotide. In a particularly preferred embodiment, NUC is 2',3'-dideoxyribonucleotide, 2',3'-dideoxy-3'-fluoro-ribonucleotide, or ribonucleotide.

Preferably, in the rigid linkage portion of the compound of Formula I, one of W and X is carbon and one of Z and Y is carbon. In an additional preferred embodiment of the rigid linkage, n is 1 or 2, o is 0, 1 or 2, and/or p is 0 or 1. More preferably, n is 1 or 2, o is 1 or 2, and p is 0 or 1. Several particularly preferred rigid linkage structures are provided immediately below:

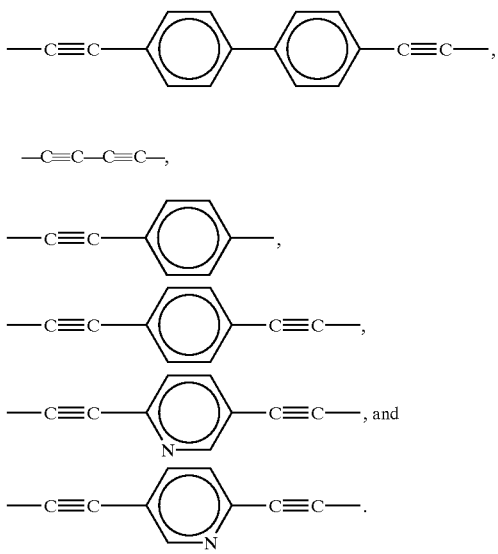

S is a spacer which serves to link the rigid linkage L and the label or member of a linkage pair LB/LG. S may add functionality to the nucleoside/nucleotide compounds, or compounds including such nucleotides, such as enhanced nuclease resistance, solubility, transport properties, hybridization, altered electrophoretic mobility, and the like. Because S is not a central feature of the invention and provides a generic function, it will be appreciated that S can have a wide variety of forms. Preferably, S is lower alkyl, lower alkylene oxide, or, amide, carbamate, sulfonamide, or any combination thereof. More preferably, S is lower alkyl or lower alkylene oxide. Most preferably, S is lower alkenyl oxide, e.g., having the structure

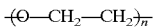

where n ranges from 1 to 8, or more preferably, wherein n is 1 or 2.

LB/LG may be any suitable label or member of a linkage pair. Where LB/LG is a member of a linkage pair, preferably the member is amino, and more preferably, the amine is a primary amine. Where LB/LG is a label, the label will include a linkage for linking the label to the spacer, S. The linkage is preferably formed by the reaction of a linking group and a complementary functionality. In a preferred embodiment, were LB/LG is a label, preferably the label is a xanthene-type dye, e.g., a rhodamine- or a fluorescein-type dye.

B. Synthesis

Three preferred alternative strategies are available for the synthesis of the nucleotides/sides of the present invention. In one approach, referred to herein as a "convergent synthesis," sub-elements of a rigid linkage, L, a spacer, S, and a linkage pair or label, LB/LG (collectively referred to herein as a "linker-arm portion") are assembled prior to their attachment to a nucleoside. Then the fully assembled linker-arm portion is attached to the nucleoside in a single reaction step. In a second approach, referred to herein as a "serial synthesis," a first element of the linker-arm portion is attached to the nucleoside followed by subsequent activation of the first element to effect the attachment of a second element of the linker-arm portion. This process is than repeated serially until all of the elements of the linker arm portion are incorporated onto the nucleotide/side. A third approach combines the strategies of both convergent and serial synthesis. That is, some elements of the linker-arm portion are pre-assembled into a multi-element intermediate, and this intermediate is then attached to an element that has already been incorporated onto the nucleoside. The preferred strategy for the preparation of a particular nucleoside/tide product depends on the convenience of the individual coupling chemistries, and their compatibility with the functional groups on the nucleotide/side.

An exemplary convergent synthesis is performed as follows. Two acetylene groups are attached to an aromatic group in two separate steps, using an aromatic precursor that includes two differentially activatable leaving groups. In a first step, a para-halophenol is coupled with a first mono-substituted acetylene, in the presence of a low-valence palladium catalyst, with displacement of the halogen atom yielding an acetylenic substituted phenol, e.g., see compounds 1 to 11 in FIG. 2. In a second step, activation of a phenolic hydroxyl as its triflate with triflic anhydride, followed by the coupling of a second mono-substituted acetylene-moiety in the presence of a low-valence palladium catalyst yields the desired structural feature, e.g., see compounds 11 to 14 in FIG. 2. If the first acetylene substituent contains a silyl protecting group, it can be removed with fluoride ion, e.g., see compounds 14 to 15 in FIG. 2. The resulting mono-substituted intermediate is then coupled with an activated nucleoside, e.g., a 5-halopyrimidine, a 8-halopurine, or a 7-halo-7-deaza-purine, in the presence of a low-valence palladium catalyst to form a protected linker nucleoside, e.g., see compounds 15 to 37 in FIG. 10.

Step-wise placement of acetylene groups onto an aromatic group can also be accomplished using an aromatic ring containing two leaving groups where the leaving group at a first position is more labile than a leaving group at a second position. Thus, for example, in 2,5-dibromopyridine, an acetylenic substitution at the 2-position with low-valence palladium catalyst will occur without effecting substitution at the 5 position. E.g., see compounds 22 to 25 in FIG. 5.

In a second method for synthesizing nucleosides/tides of the present invention a serial synthetic technique is employed. E.g, for a linker-arm portion containing multiple acetylene units, an addition of a first mono-substituted acetylene group to an activated nucleoside is performed as described above, e.g., see compounds 33 to 42 in FIG. 15. Next, after deprotection of the first acetylene group, an additional mono-substituted acetylene group is coupled to the first acetylene using cuprous chloride and oxygen, e.g., see compounds 42 to 44 in FIG. 15. Alternatively, an aromatic ring may be added using a low-valence palladium catalyst as described above. Additional acetylene groups or aromatic rings may be added by repetition of these synthetic steps.

In a third method for synthesizing nucleosides/tides of the present invention, the product is prepared using a combination of serial and convergent synthetic techniques. E.g., an aromatic ring containing a leaving group, and an acetylene group in para-position with respect to the leaving group, can be prepared using a para-halophenol and a mono-substituted acetylene group as described in the first method. A mono-substituted acetylenic nucleotide/side can be prepared as described in the second method. Then, the acetylene is coupled to this intermediate using a low-valence palladium catalyst as described above yielding the desired product.

III. Methods of Using the Nucleotide Compounds

In a preferred category of methods referred to herein as "fragment analysis" or "genetic analysis" methods, labeled polynucleotide fragments are generated through template-directed enzymatic synthesis, e.g., a polymerase-directed primer extension reaction. Specifically, the invention includes a method for performing such a primer extension reaction comprising the steps of (1) providing a template nucleic acid, (2) annealing an oligonucleotide primer to a portion of the template nucleic acid for forming a primer-template hybrid, and (3) adding primer-extension reagents to the primer-template hybrid for extending the primer, the primer extension reagents including a nucleotide compound having the structure of the nucleotide compounds of Formula I.

Preferably, in the primer extension method of the present invention, the primer extension reagent includes a thermostable polymerase, e.g., rTth DNA polymerase, BST DNA polymerase, Vent DNA polymerase, Pfu DNA polymerase, or Taq polymerase enzyme, e.g. *PCR Primer: A Laboratory Manual*, Dieffenbach and Dveksler, eds., CSHL Press (1995). More preferably, the thermostable polymerase is Taq DNA polymerase, or a mutant Taq polymerase enzyme having a mutation at the F667 position, e.g., Tabor and Richardson, EP 0 655 506. More preferably, the mutation is F667Y. In an additional preferred embodiment of the primer extension reaction of the present invention, the Taq polymerase enzyme is a mutant that includes, in addition to the F667Y mutation, mutations at the 660, 664, 665 and/or the 681 position. See U.S. patent application Ser. No. 09/041,878, filed Mar. 12, 1998. Preferred mutations at these positions include R660D, R660E, R660C, R660S, R660P, and E681G. In a particularly preferred embodiment, the mutant Taq polymerase enzyme includes the mutations R660C or R660S, R660P and F667Y.

Subsequent to a primer extension reaction, the fragments may be subjected to a size-dependent separation process, e.g., electrophoresis or chromatography, or hybridization to a set of polynucleotide probes which bind to the fragments in a sequence-dependent manner, e.g., Drmanac et al., *Nature Biotechnology*, 16: 54–58 (1998), Ramsay, *Nature Biotechnology*, 16: 40–44 (1998), and U.S. Pat. No. 5,202,231. In a preferred embodiment, subsequent to separation or hybridization, the fragments are detected, e.g., by laser-induced fluorescence. In a particularly preferred embodiment, multiple classes of polynucleotides are separated or hybridized simultaneously and the different classes are distinguished by spectrally resolvable labels.

In a particularly preferred fragment analysis method, classes identified in accordance with the invention are defined in terms of terminal nucleotides so that a correspondence is established between the four possible terminal bases and the members of a set of differentially detectable labels. E.g, when spectrally-resolvable fluorescent labels are used, such sets are readily assembled by measuring emission and absorption bandwidths with commercially available spectrophotometers. More preferably, the classes arise in the context of the chemical or chain termination methods of DNA sequencing, and most preferably the classes arise in the context of the chain termination methods, i.e., dideoxy DNA sequencing, or Sanger-type sequencing.

Sanger-type sequencing involves the synthesis of a DNA strand by a DNA polymerase in vitro using a single-stranded or double-stranded DNA template whose sequence is to be determined. Synthesis is initiated at a defined site based on where an oligonucleotide primer anneals to the template. The synthesis reaction is terminated by incorporation of a nucleotide analog that will not support continued DNA elongation. Exemplary chain-terminating nucleotide analogs include the 2',3'-dideoxynucleoside 5'-triphosphates (ddNTPs) which lack a 3'-OH group necessary for 3' to 5' DNA chain elongation. When proper proportions of dNTPs (2'-deoxynucleoside 5'-triphosphates) and one of the four ddNTPs are used, enzyme-catalyzed polymerization will be terminated in a fraction of the population of chains at each site where the ddNTP is incorporated. If fluorescently labeled primers or labeled ddNTPs are used for each reaction, the sequence information can be detected by fluorescence after separation by high-resolution electrophoresis. In the chain termination method, nucleotides of the invention can be used to form labeled dideoxynucleotides.

Where the primer-extension fragments are subjected to a size-dependent separation process, preferably they are separated by electrophoretic procedures, e.g., Gould and Matthews, cited above; Rickwood and Hames, Eds., *Gel Electrophoresis of Nucleic Acids: A Practical Approach*, IRL Press Limited, London, 1981; Osterman, *Methods of Protein and Nucleic Acid Research, Vol.* 1 Springer-Verlag, Berlin, 1984; or U.S. Pat. Nos. 5,374,527, 5,624,800 and/or 5,552,028. Preferably the type of electrophoretic matrix is crosslinked or uncrosslinked polyacrylamide having a concentration (weight to volume) of between about 2–20 weight percent. More preferably, the polyacrylamide concentration is between about 4–8 percent. Preferably in the context of DNA sequencing in particular, the electrophoresis matrix includes a denaturing agent, e.g., urea, formamide, and the like. Detailed procedures for constructing such matrices are given by Maniatis et al., "Fractionation of Low Molecular Weight DNA and RNA in Polyacrylamide Gels Containing 98% Formamide or 7 M Urea," in *Methods in Enzymology*, 65: 299–305 (1980); Maniatis et al., "Chain Length Determination of Small Double- and Single-Stranded DNA Molecules by Polyacrylamide Gel Electrophoresis," *Biochemistry*, 14: 3787–3794 (1975); Maniatis et al., *Molecular Cloning: A Laboratory Manual*, Cold Spring Harbor Laboratory, New York, pgs. 179–185 (1982); and ABI PRISM™ 377 *DNA Sequencer User's Manual, Rev. A*, January 1995, Chapter 2 (p/n 903433, The Perkin-Elmer Corporation, Foster City, Calif.). The optimal electrophoresis conditions, e.g., polymer concentration, pH, temperature, concentration of denaturing agent, employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations.

Subsequent to electrophoretic separation, the labeled polynucleotide fragments are detected, e.g., by measuring the fluorescence emission. Exemplary fluorescence-based electrophoresis detection systems are described elsewhere, e.g., U.S. Pat. Nos. 5,543,026; 5,274,240; 4,879,012; 5,091,652 and 4,811,218.

13

IV. EXAMPLES

The invention will be further clarified by a consideration of the following examples, which are intended to be purely exemplary of the invention and not to in any way limit its scope.

Materials and Methods

Thin layer chromatography (TLC) was conducted on glass plates precoated with 250 μm layers of silica gel 60-$F_{254}$; the compounds were located by quenching of fluorescence and/or by charring with 5% sulfuric acid. Unless otherwise indicated, all purifications were carried out by flash column chromatography performed on SIP brand silica gel 60 Å (230–400 Mesh ASTM). $^1$H NMR spectra were recorded at 300 MHz on solutions dissolved in $CDCl_3$ (internal $Me_4Si$, δ0) or $D_2O$ (external $Me_4Si$, δ0) at ambient temperature. $^{13}$C NMR spectra were recorded at 75.5 MHz, $^{19}$F NMR spectra were recorded at 282.23 MHz on solution dissolved in $CDCl_3$ or $D_2O$, and $^{31}$p NMR spectra were recorded at 121.44 MHz on solutions dissolved in $D_2O$. In all cases, observed NMR data were in accord with the indicated structures. The product purity was analyzed by analytical HPLC. Unless otherwise indicated, all reactions were carried out at ambient temperatures, and in the work-up, solutions in organic solvents were washed with equal volumes of aqueous solutions. Organic solutions were dried (anhydrous $Na_2SO_4$) prior to concentration on a rotary evaporator under the vacuum of a water aspirator with bath temperature of 40–50°.

Anion-exchange high-performance chromatography (AE-HPLC) was performed as follows. Column: Aquapore™ AX-300, 7 μm particle size, 220×4.6 mm (PE Applied Biosystems); gradient: 40% acetonitrile: 60% triethylammonium bicarbonate (TEAB, 0.1M) to 40% acetonitrile: 60% TEAB (1.5 M) at 1.5 ml/min over 20 min, followed by isocratic elution; detection: UV absorbance at 260 nm.

Reverse phase high-performance chromatography (RP-HPLC) was performed as follows. Column: Spheri-5 RP-C18, 5 gm particle size, 220×4.6 mm (PE Applied Biosystems); gradient: 100% triethylammonium acetate (TEAA, 0.1M) to 40% acetonitrile 60% TEAA at 1.5 ml/min over 20 min followed by 40% to 100% acetonitrile at 1.5 mL/min over 5 min.

Example 1

Figure 8:
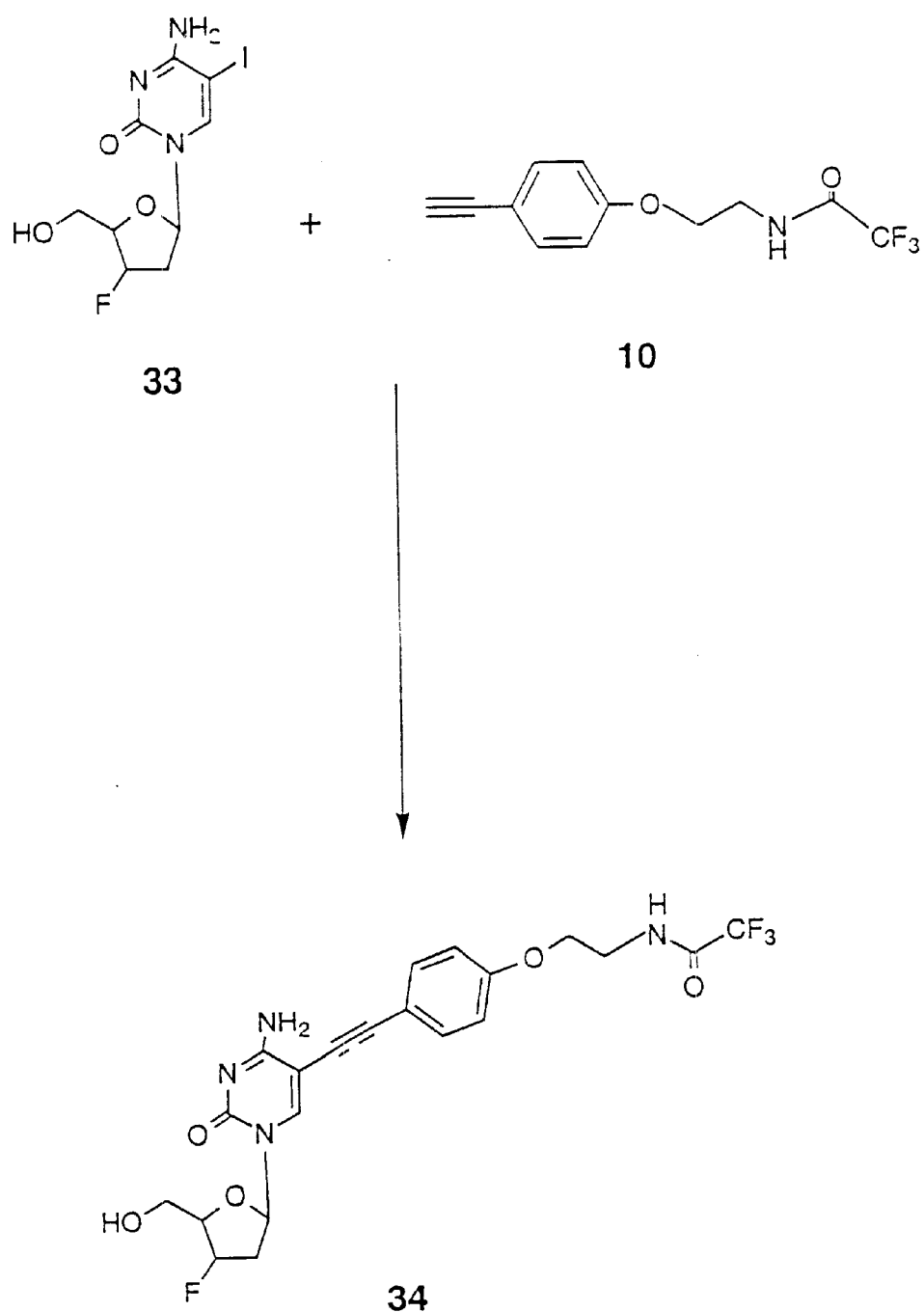
FIG. 8 shows the synthesis of compound 34 of the present invention.

Synthesis of Nucleoside-Protected-Linker Compound 34 (See FIGS. 1 and 8)

To a stirred solution of 1 (1 eq.) in N,N-dimethylformamide was added NaH (1.2 eq., 80%) portion-wise. After complete NaH addition, stirring was continued for 0.5 h at room temperature, then the reaction was cooled to 0° C. Bromide 2 (2 eq.) was added, and stirring was continued for 0.5 h at 0° C., followed by stirring at room temperature for 2 h. After careful addition of methanol to decompose excess NaH, the solvent was evaporated and the crude product was purified by flash column chromatography to give 3 as a solid.

To a solution of 3 (1 eq.) in pyridine (15 mL) was added methanesulfonyl chloride (2 eq.) and stirred for 1 h at 0° C. then at room temperature for 12 h. The mixture was then concentrated and purified by flash column chromatography to give 4.

To a solution of 4 (1 eq.) in N,N-dimethylformamide was added potassium phthalamide 5 (1.5 eq.). After stirring for 12 h at 70° C., the mixture was concentrated and then diluted with dichloromethane (100 mL). After removal of the solid by filtration, the organic layer was washed with water, dried, and concentrated. The residue was purified by flash column chromatography to give 6.

A mixture of 6 (1 eq.) and ethylenediamine (9.6 eq.) was heated at 80° C. in ethanol (4 mL) for 1 h. The reaction mixture was then evaporated to dryness, the residue was dissolved in N,N-dimethylformamide (2 mL) and methyl trifluoroacetate (6.5 mL) was added. After stirring for 1 h at 80° C., solvent was evaporated and residue was purified by flash column chromatography to give 7.

Compound 7 (1 eq.) was reacted with (triethylsilyl) acetylene 8 (5 eq.) in the presence of cuprous iodide (0.2 eq.), tetrakis(triphenylphosphine)palladium (0.2 eq.) and triethylamine (2 eq.) in N,N-dimethylformamide for 12 h at room temperature under Argon. The reaction is then concentrated and purified by flash column chromatography to give 9.

To a solution of 9 (0.6 mmoles) in anhydrous oxolane (9 mL) was added 1M tetrabutylammonium fluoride in oxolane (4.5 mL), and the mixture was stirred for 2 h at 0° C. After concentration the residue was purified by flash column chromatography providing 10.

3' Fluoro-5-iodo-2',3'-dideoxycytidine 33 (1 eq.) was reacted with linker 10 (4 eq.) in the presence of cuprous iodide (0.2 eq.), tetrakis(triphenylphosphine)palladium (0.2 eq.) and triethylamine (2 eq.) in N,N-dimethylformamide for 12 h at room temperature under Argon. The reaction was concentrated and purified by flash column chromatography to give 34.

Example 2

Figure 9:
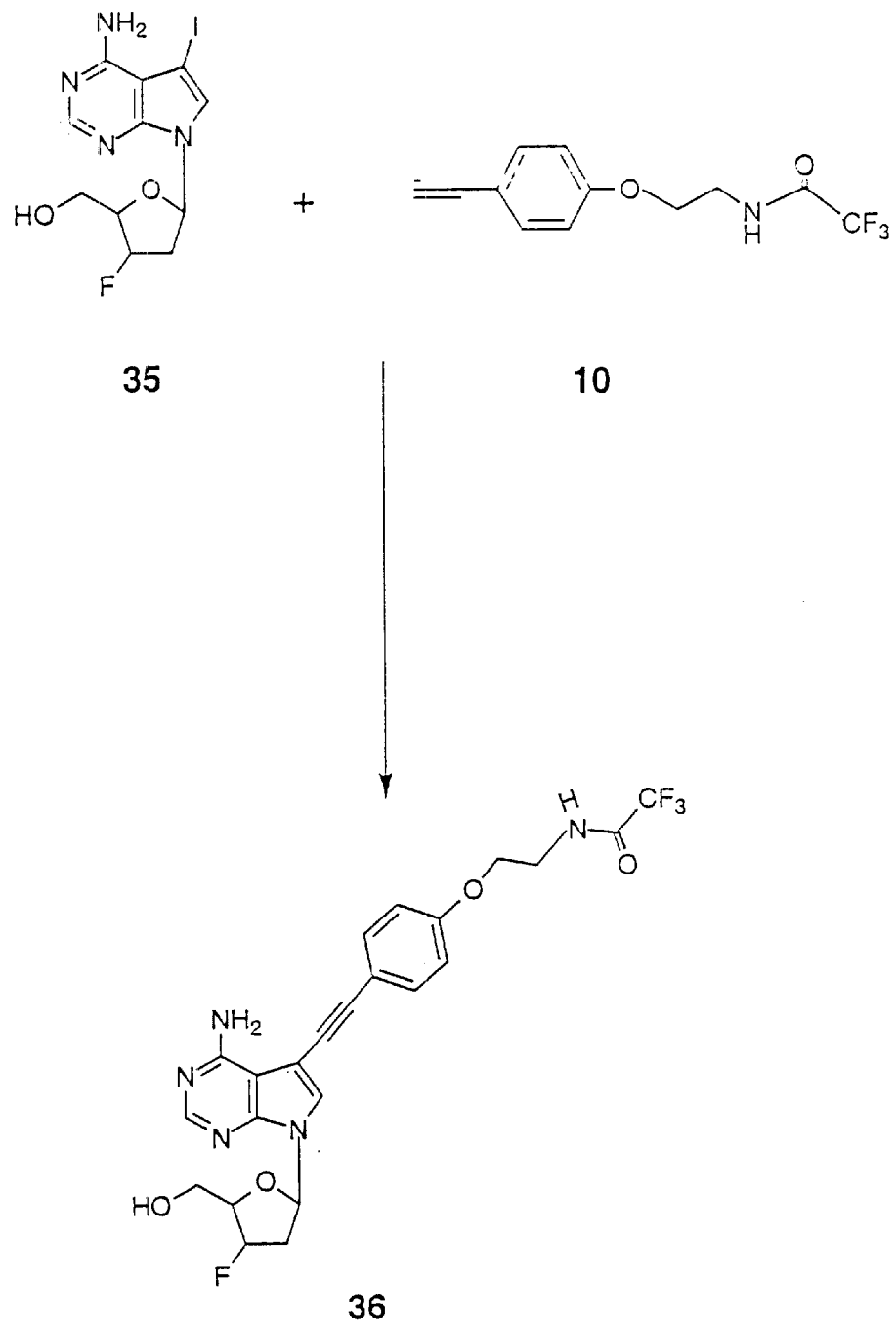
FIG. 9 shows the synthesis of compound 36 of the present invention.

Synthesis of Nucleoside-Protected-Linker Compound 36 (See FIG. 9)

3' Fluoro-7-deaza-7-Iodo-2',3'-dideoxyadenosine 35 (1 eq.) was reacted with linker 10 (4 eq.) in the presence of cuprous iodide (0.2 eq.), tetrakis(triphenylphosphine) palladium (0.2 eq.) and triethylamine (2 eq.) in N,N-dimethylformamide for 12 h at room temperature under Argon. The reaction was then concentrated and purified by flash column chromatography to give 36.

Example 3

Figure 2:
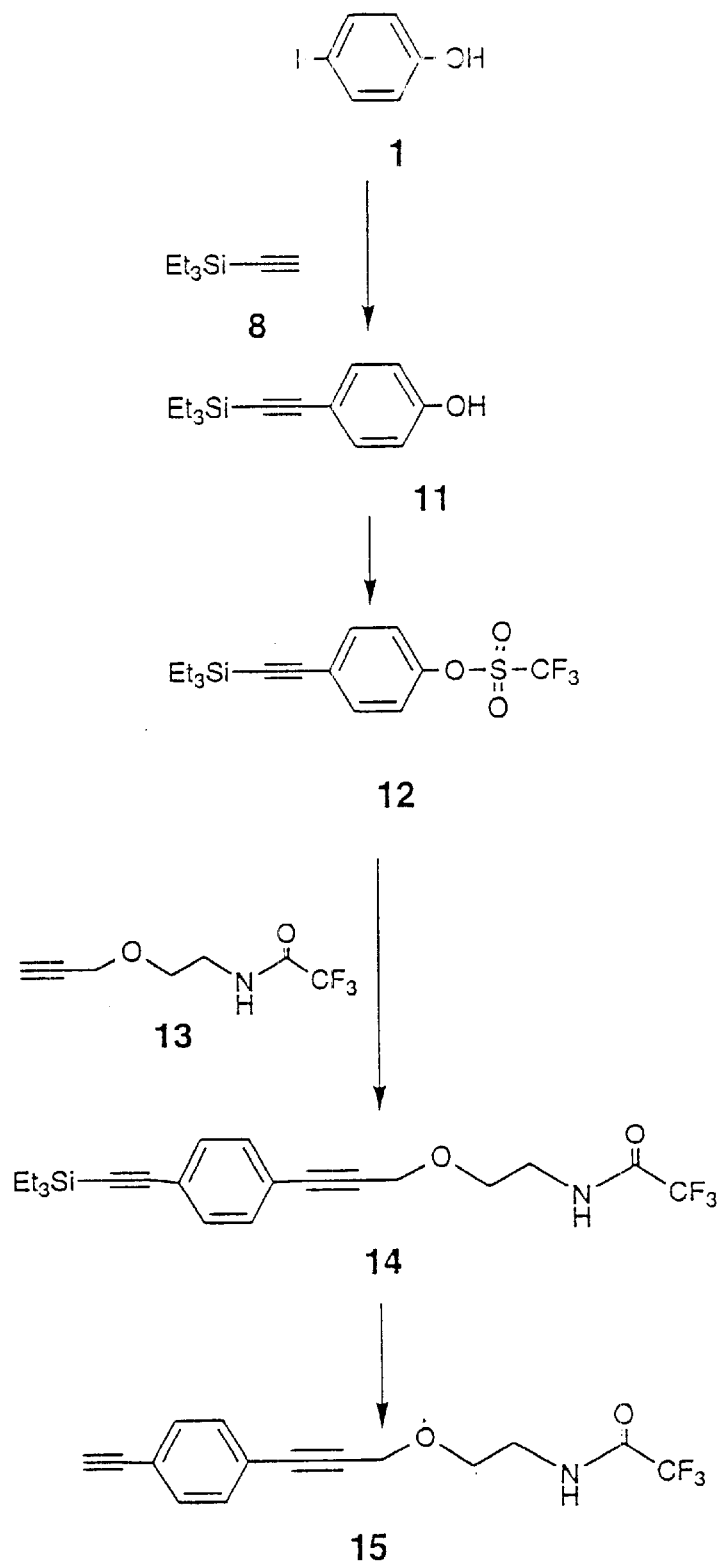
FIG. 2 shows the synthesis of compound 15 of the present invention.
Figure 10:
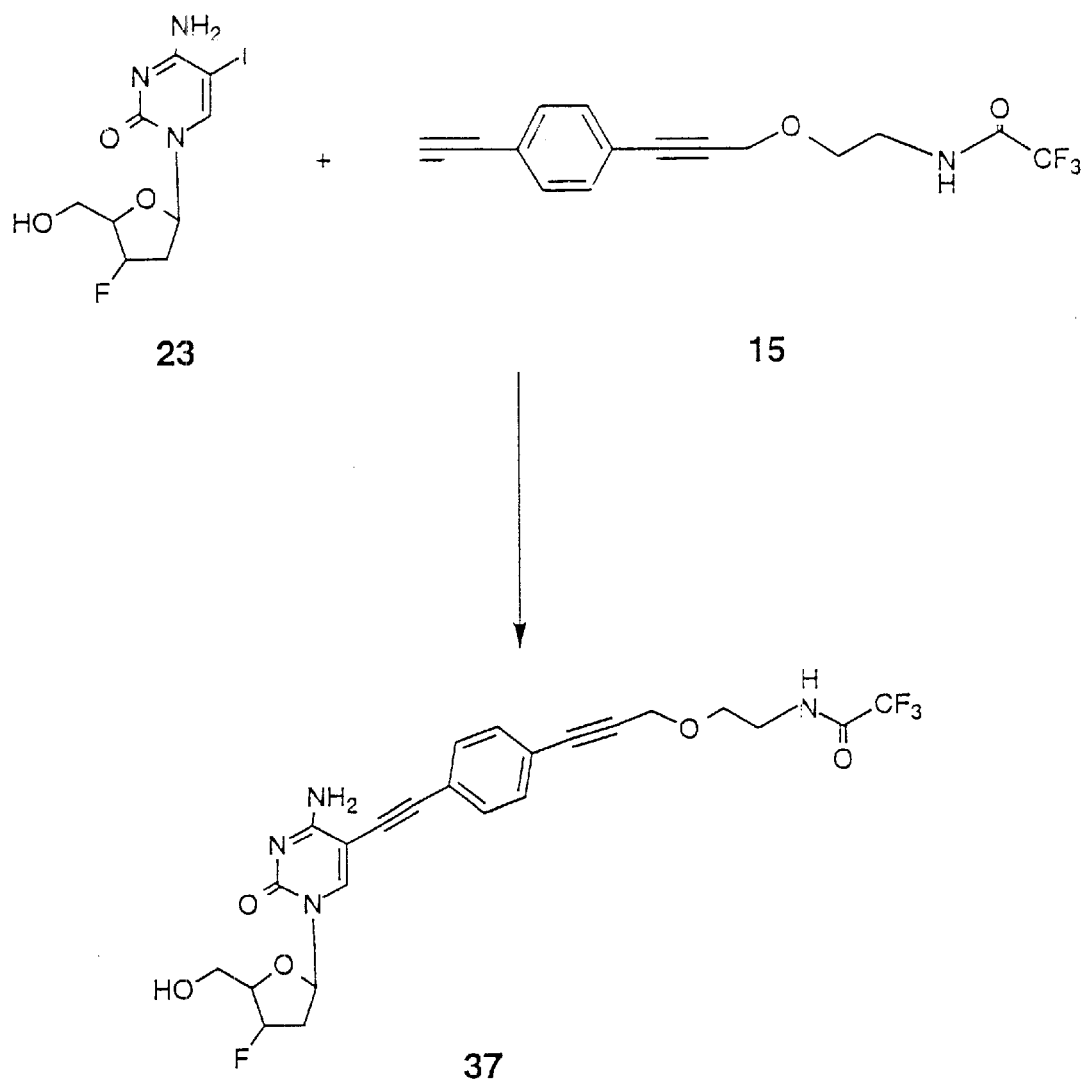
FIG. 10 shows the synthesis of compound 37 of the present invention.
Figure 11:
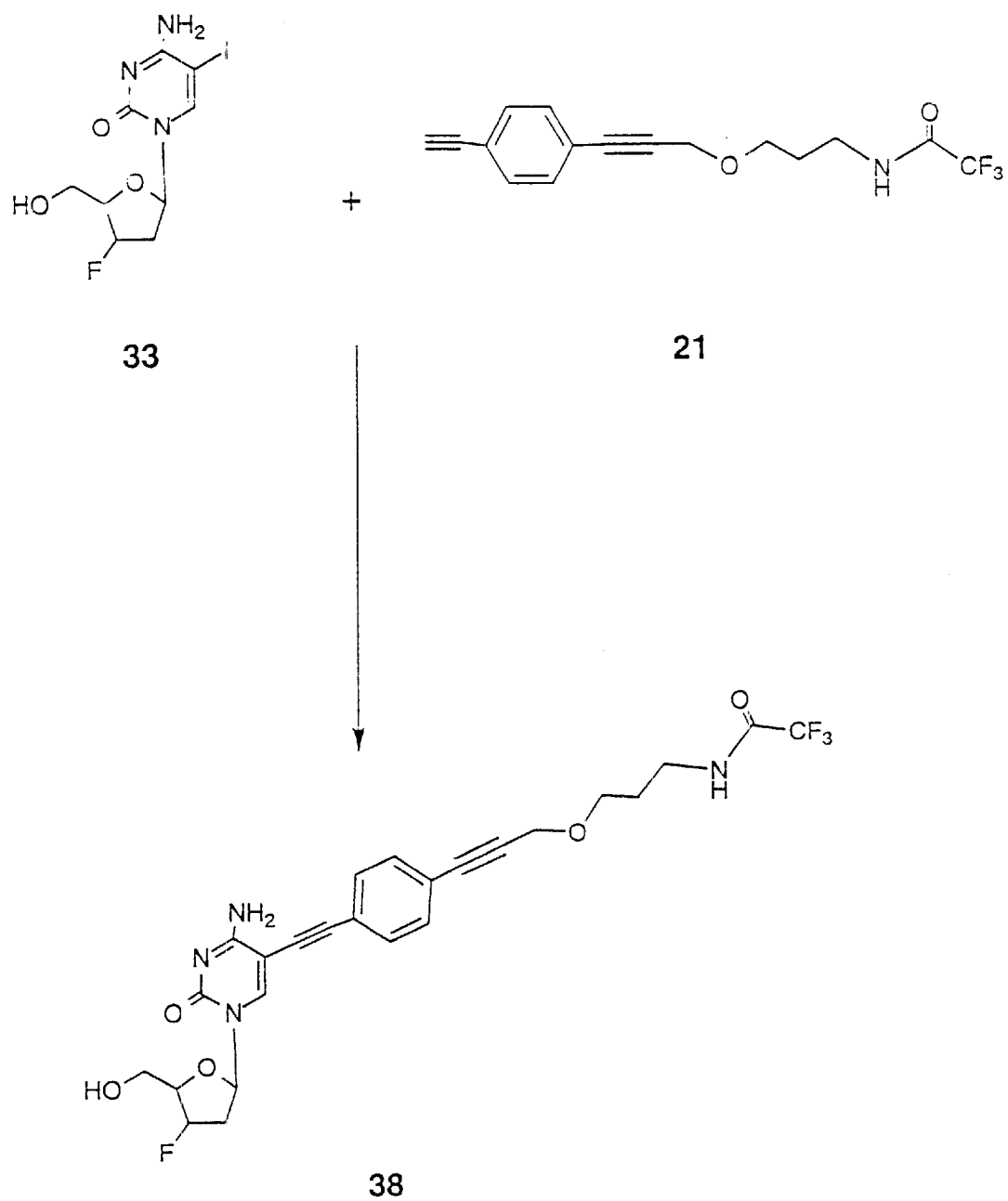
FIG. 11 shows the synthesis of compound 38 of the present invention.

Synthesis of Nucleoside-Protected-Linker Compound 37 (See FIGS. 2 and 10)

4-Iodophenol 1 (1 eq.) was reacted with (triethylsilyl) acetylene 8 (4 eq.) in the presence of cuprous iodide (0.2 eq.), tetrakis(triphenylphosphine)palladium (0.2 eq.) and triethylamine (2 eq.) in N,N-dimethylformamide for 12 h at room temperature under Argon. The reaction was then concentrated and purified by flash column chromatography to give 11.

To a stirred solution of 11 (1 eq.) in dichloromethane (50 mL) at −40° C. was added trifluoromethanesulfonic anhydride (1.2 eq.) followed by triethyl amine (1.2 eq.) under Argon. Stirring was continued for an additional 1 h at −40° C., then the reaction mixture was warmed up to room temperature and stirred for 5 h. The reaction mixture was diluted with dichloromethane and successively washed with aq. dil. $H_2SO_4$, sat. $NaHCO_3$ solution, brine, and water, dried, concentrated and purified by flash column chromatography to give 12.

Compound 12 (1 eq.) was reacted with linker 13 (4 eq.) in the presence of cuprous iodide (0.2 eq.), tetrakis (triphenylphosphine)palladium (0.2 eq.) and triethylamine (2 eq.) in N,N-dimethylformamide for 12 h at room temperature under Argon. The reaction was then concentrated and purified by flash column chromatography to give 14.

To a solution of 14 (0.46 mmoles) in anhydrous oxolane (5 mL) was added 1M tetrabutylammonium fluoride in oxolane (1.5 mL), and the mixture was stirred for 2 h at 0° C. After concentration the residue was purified by flash column chromatography providing 15.

3'-Fluoro-5-iodo-2',3'-dideoxycytidine 33 (1 eq.) was reacted with linker 15 (4 eq.) in the presence of cuprous iodide (0.2 eq.), tetrakis(triphenylphosphine)palladium (0.2 eq.) and triethylamine (2 eq.) in N,N-dimethylformamide for 12 h at room temperature under Argon. The reaction was concentrated and purified by flash column chromatography to give 37.

Example 4

Figure 3:
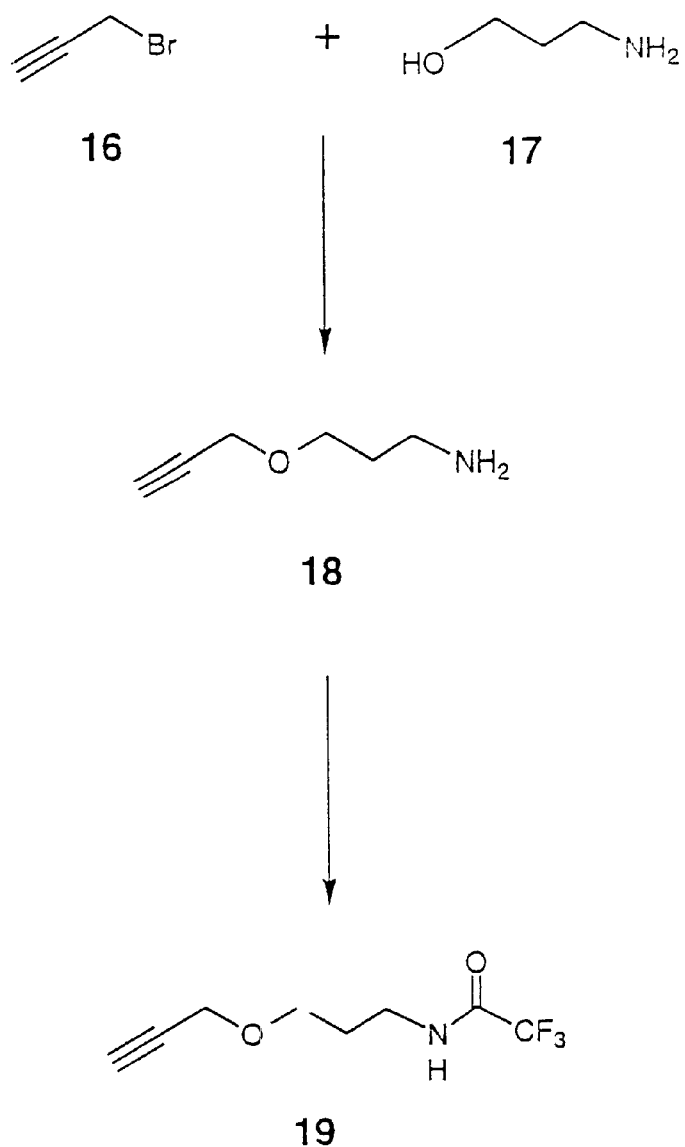
FIG. 3 shows the synthesis of compound 19 of the present invention.
Figure 4:
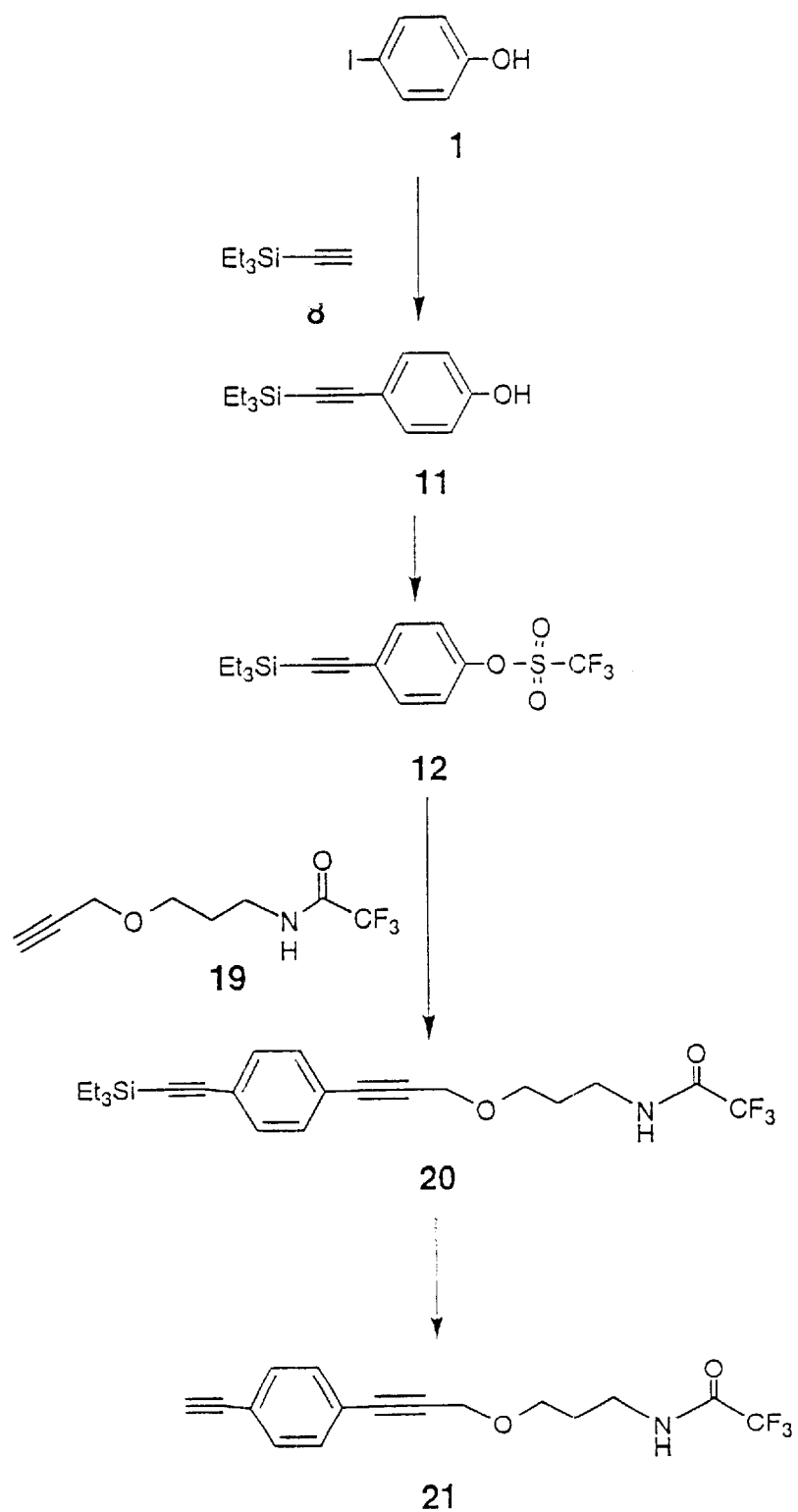
FIG. 4 shows the synthesis of compound 21 of the present invention.

Synthesis of Nucleoside-Protected-Linker Compound 38 (See FIGS. 3, 4 and 9)

To a stirred solution of NaH (1.05 eq., 95%/o) in oxolane was added 17 (1 eq.) dropwise at 0° C. After complete addition, stirring was continued for 1 h at 0° C., then bromide 16 (1.05 eq.) was added over a period of 2 h, and stirring was continued for 2 h at 0° C, followed by stirring at room temperature for 24 h. After careful addition of methanol to decompose excess NaH, the solvent was evaporated and the crude product was purified by fraction distillation to give 18.

Compound 18 was reacted with large excess of methyl trifluoroacetate at room temperature for 12 h. Solvent was evaporated and residue was purified by flash column chromatography to give 19.

Compound 12 (1 eq.) was reacted with linker 19 (4 eq.) in the presence of cuprous iodide (0.2 eq.), tetrakis (triphenylphosphine)palladium (0.2 eq.) and triethylamine (2 eq.) in N,N-dimethylformamide for 12 h at room temperature under Argon. The reaction was then concentrated and purified by flash column chromatography to give 20.

To a solution of 20 (3.35 mmoles) in anhydrous oxolane (20 mL) was added 1M tetrabutylammonium fluoride in oxolane (10 mL), and the mixture was stirred for 3 h at room temperature. After concentration the residue was purified by flash column chromatography providing 21.

3'-Fluoro-5-iodo-2',3'-dideoxycytidine 33 (1 eq.) was reacted with linker 21 (4 eq.) in the presence of cuprous iodide (0.2 eq.), tetrakis(triphenylphosphine)palladium (0.2 eq.) and triethylamine (2 eq.) in N,N-dimethylformamide for 12 h at room temperature under Argon. The reaction was then concentrated and purified by flash column chromatography to give 38.

Example 5

Figure 5:
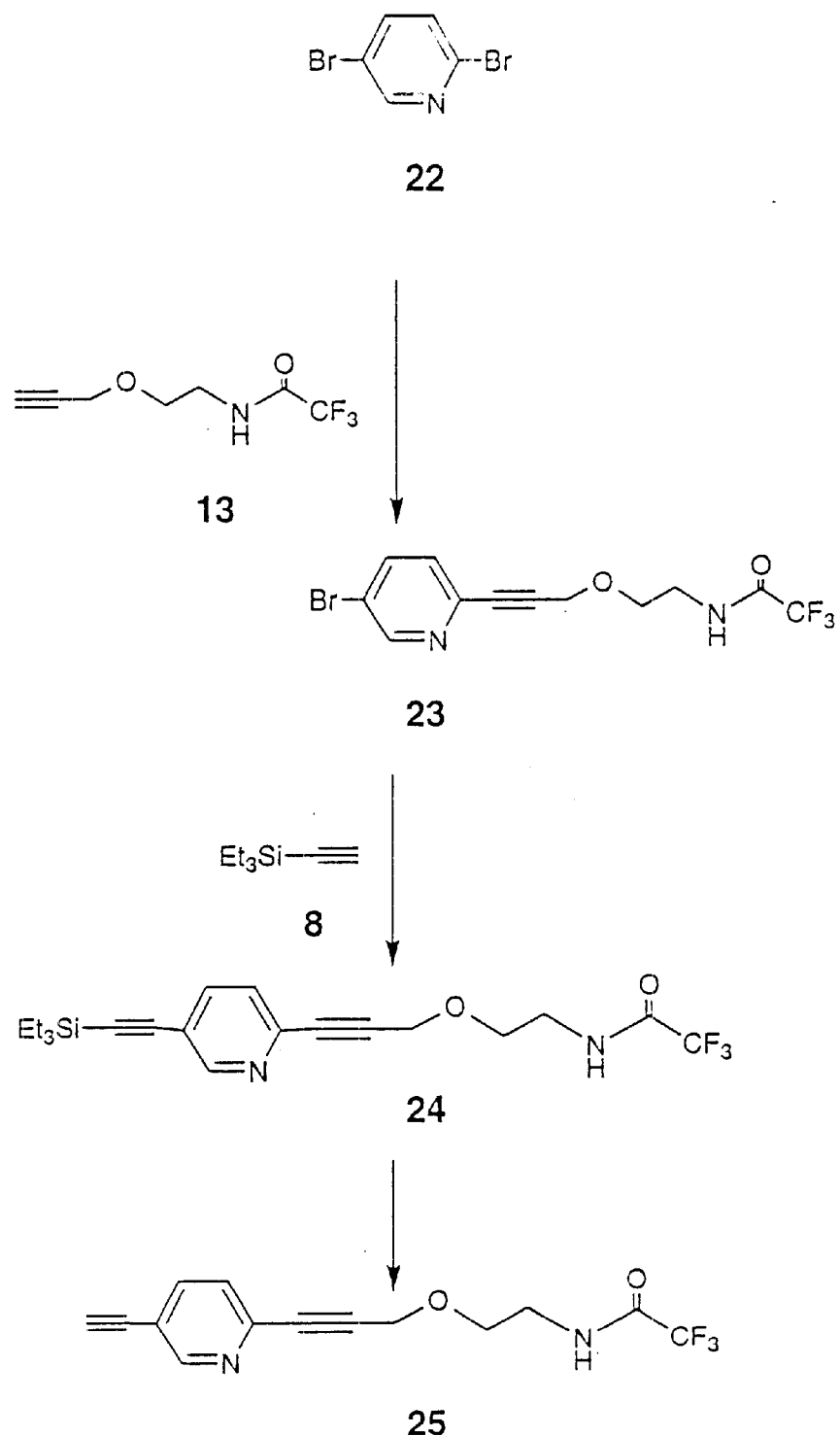
FIG. 5 shows the synthesis of compound 25 of the present invention.
Figure 12:
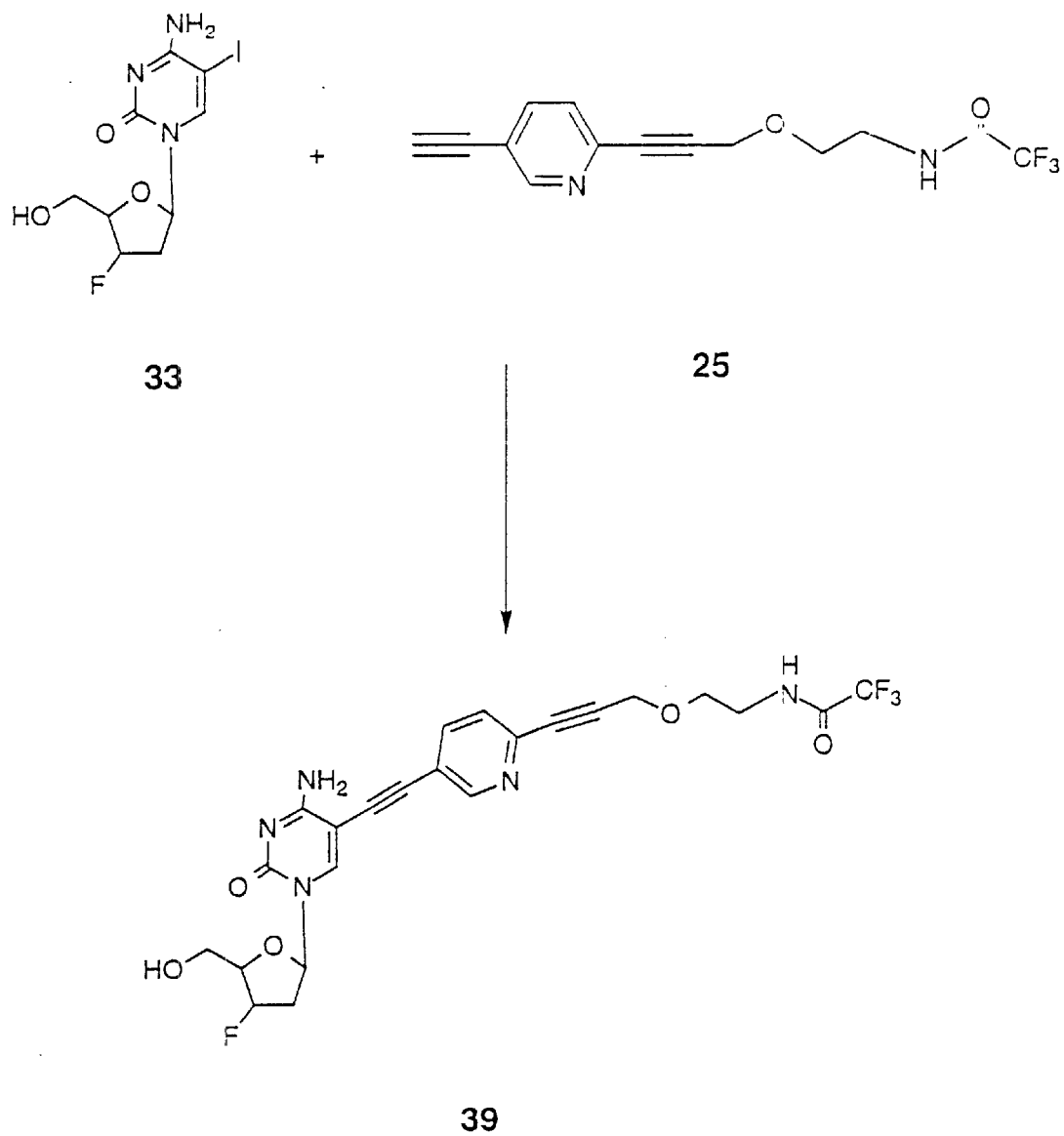
FIG. 12 shows the synthesis of compound 39 of the present invention.

Synthesis of Nucleoside-Protected-Linker Compound 39 (See FIGS. 5 and 12)

2,5-Dibromopyridine 22 (1 eq.) was reacted with linker 13 (1.05 eq.) in the presence of cuprous iodide (0.02 eq.), and bis(triphenylphosphinyl)palladium dichloride (0.02 eq.) in triethylamine (30 mL) for 12 h at room temperature under Argon. The reaction was then diluted with dichloromethane and washed with brine solution, dried, filtered, and concentrated. The concentrate was purified by flash column chromatography to give 23.

Compound 23 (1 eq.) was reacted with (triethylsilyl)acetylene 8 (2 eq.) in the presence of cuprous iodide (0.05 eq.), tetrakis(triphenylphosphine)palladium (0.05 eq.) and triethylamine (10 eq.) in N,N-dimethylformamide for 12 h at room temperature under Argon. The reaction is then concentrated and purified by flash column chromatography to give 24.

To a solution of 24 (0.5 mmoles) in anhydrous oxolane (10 mL) was added 1M tetrabutylammonium fluoride in oxolane (1.5 mL), and the mixture was stirred for 2 h at 0° C. After concentration the residue was purified by flash column chromatography providing 25.

3'-Fluoro-5-iodo-2',3'-dideoxycytidine 33 (1 eq.) was reacted with linker 25 (4 eq.) in the presence of cuprous iodide (0.2 eq.), tetrakis(triphenylphosphine)palladium (0.2 eq.) and triethylamine (2 eq.) in N,N-dimethylformamide for 12 h at room temperature under Argon. The reaction was then concentrated purified by flash column chromatography to give 39.

Example 6

Figure 6:
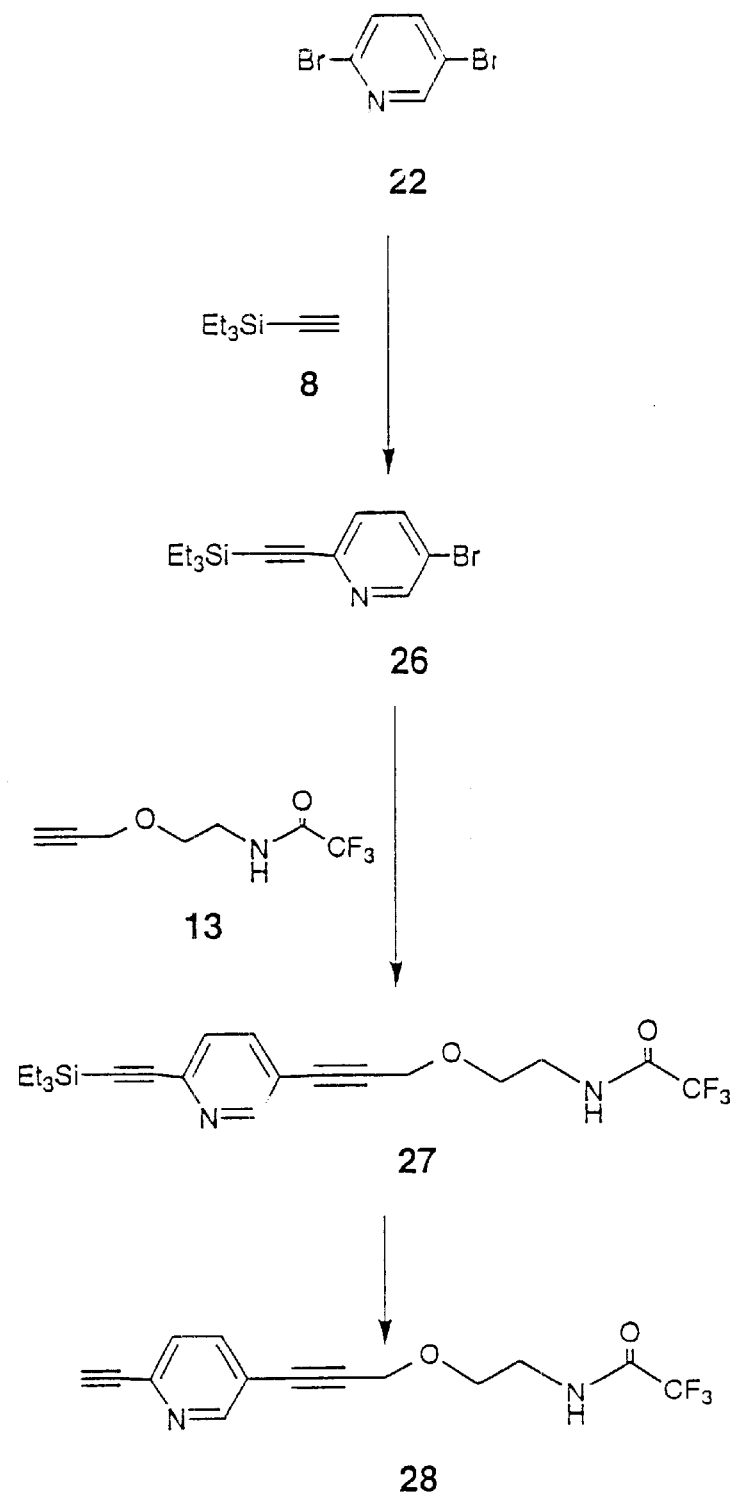
FIG. 6 shows the synthesis of compound 28 of the present invention.
Figure 13:
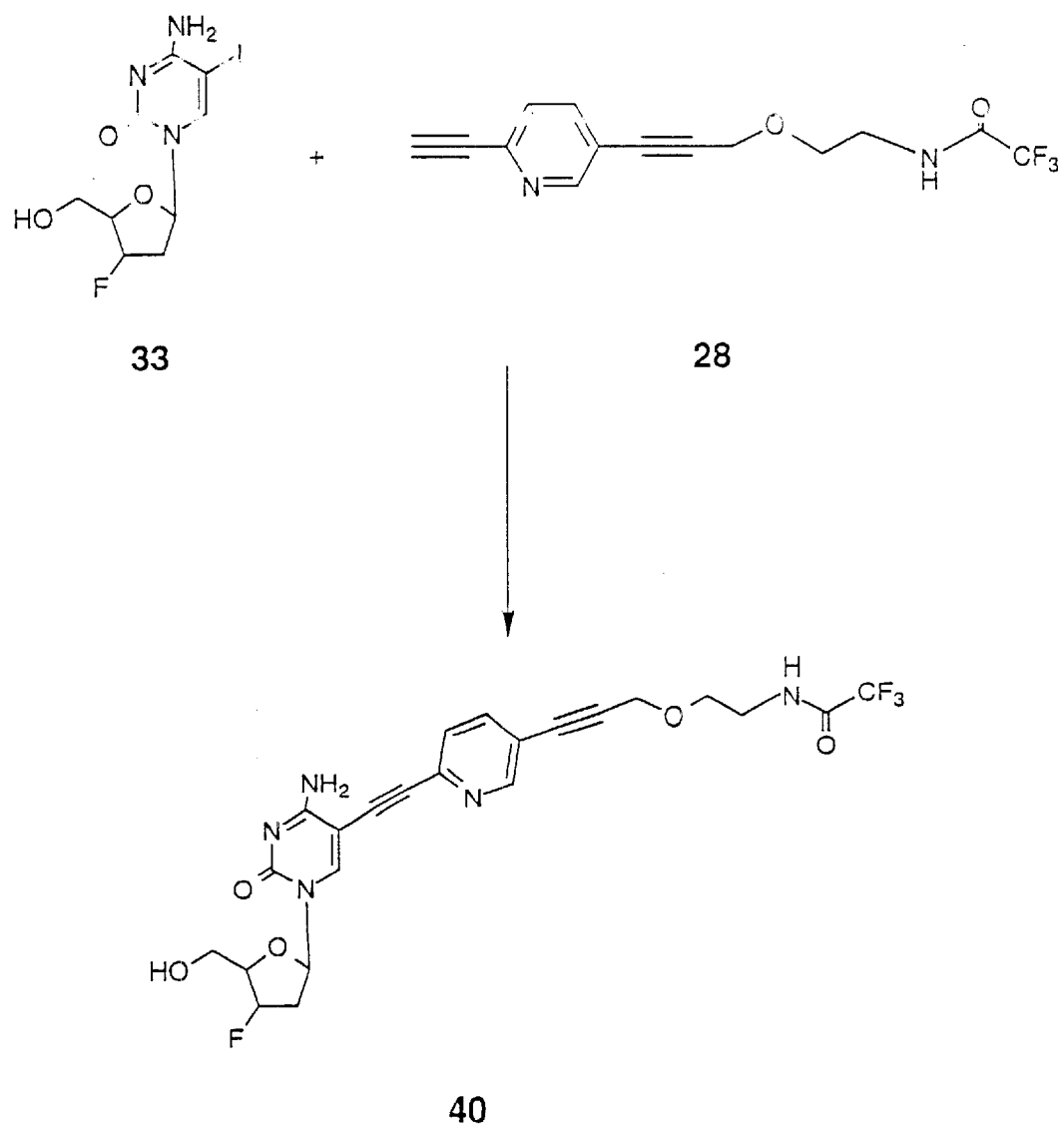
FIG. 13 shows the synthesis of compound 40 of the present invention.

Synthesis of Nucleoside-Protected-Linker Compound 40 (See FIGS. 6 and 13)

2,5-Dibromopyridine 22 (1 eq.) was reacted with (triethylsilyl)acetylene 8 (1.05 eq.) in the presence of cuprous iodide (0.02 eq.), and bis(triphenylphosphinyl)palladium dichloride (0.02 eq.) in triethylamine (75 mL) at 0° C. for 1 h, then the reaction mixture was warmed up to room temperature and stirred for 12 h at that temperature under Argon. The reaction was then diluted with dichloromethane and washed with brine solution, dried, filtered, and concentrated. The concentrate was purified by flash column chromatography to give 26.

Compound 26 (1 eq.) was reacted with linker 13 (2 eq.) in the presence of cuprous iodide (0.05 eq.), tetrakis(triphenylphosphine)palladium (0.05 eq.) and triethylamine (10 eq.) in N,N-dimethylformamide for 12 h at room temperature under Argon. The reaction is then concentrated and purified by flash column chromatography to give 27.

To a solution of 27 (0.5 mmoles) in anhydrous oxolane (10 mL) was added 1M tetrabutylammonium fluoride in oxolane (1.5 mL), and the mixture was stirred for 2 h at 0° C. After concentration the residue was purified by flash column chromatography providing 28.

3'-Fluoro-5-iodo-2',3'-dideoxycytidine 33 (1 eq.) was reacted with linker 28 (3 eq.) in the presence of cuprous iodide (0.05 eq.), tetrakis(triphenylphosphine)palladium (0.05 eq.) and triethylamine (2 eq.) in N,N-dimethylformamide for 12 h at room temperature under Argon. The reaction was then concentrated and purified by flash column chromatography to give 40.

Example 7

Figure 7:
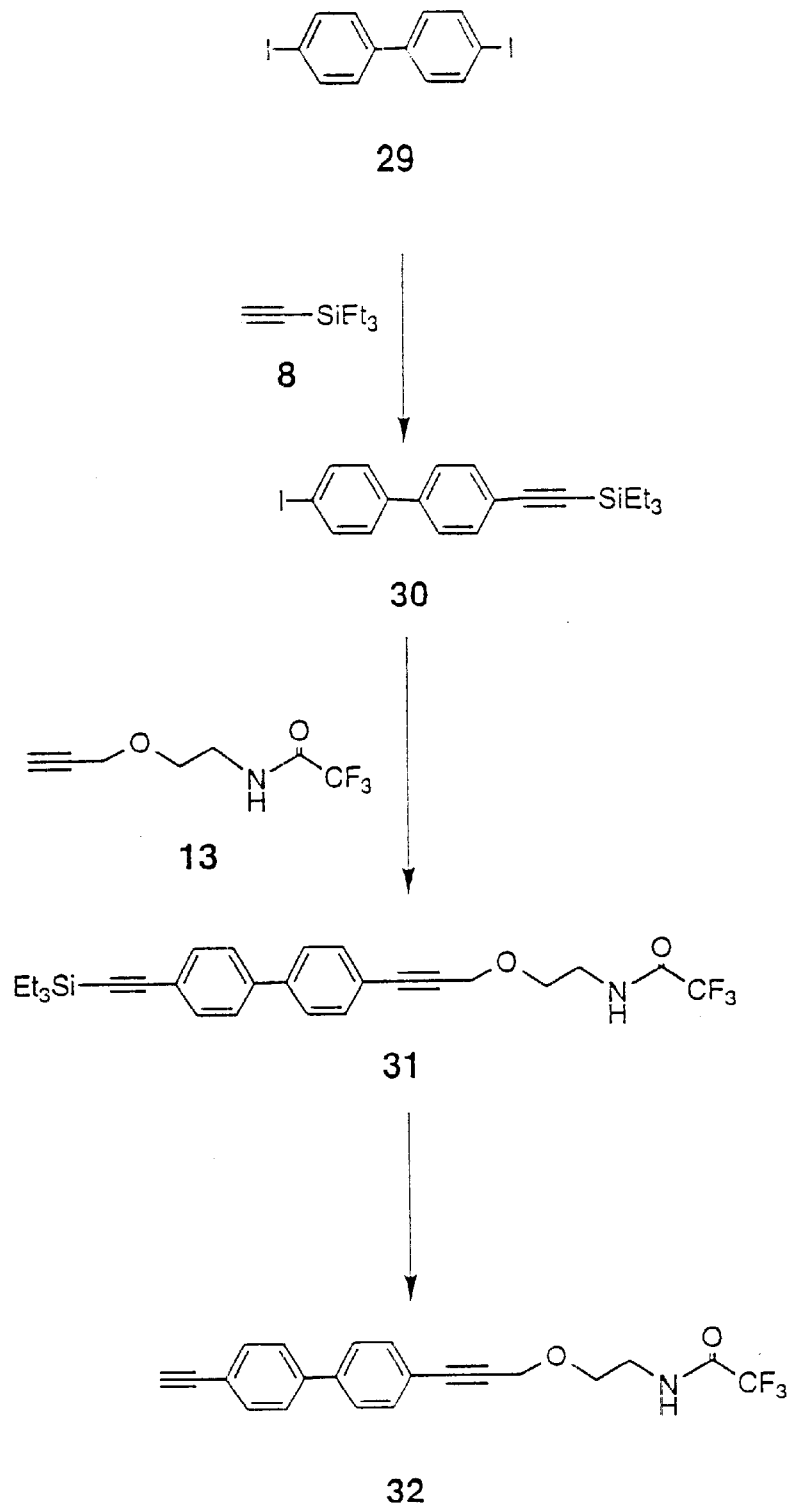
FIG. 7 shows the synthesis of compound 32 of the present invention.
Figure 14:
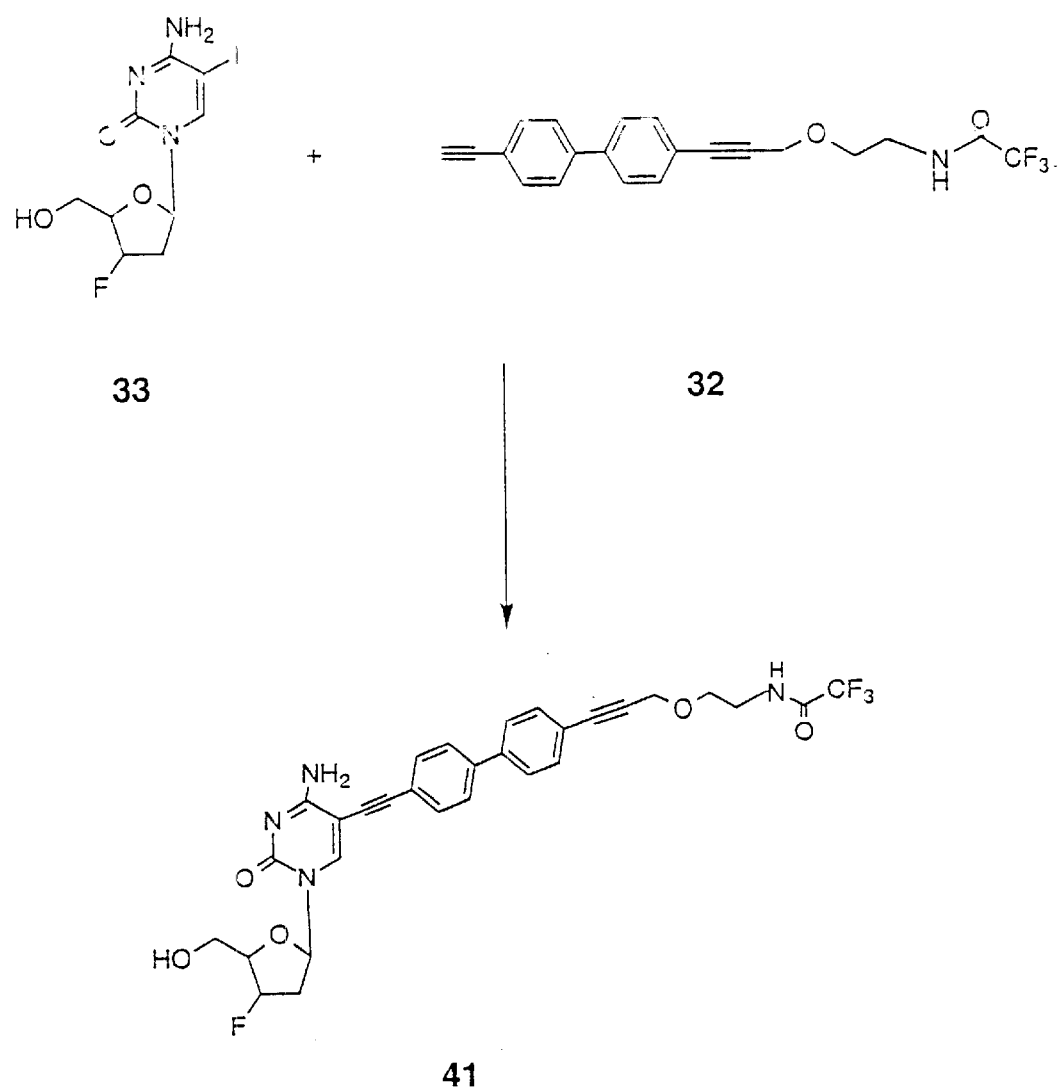
FIG. 14 shows the synthesis of compound 41 of the present invention.

Synthesis of Nucleoside-Protected-Linker Compound 41 (See FIGS. 7 and 14)

4,4'-Diiodobiphenyl 29 (1 eq.) was reacted with (triethylsilyl)acetylene 8 (2 eq.) in the presence of cuprous iodide (0.2 eq.), tetrakis(triphenylphosphine)palladium (0.2 eq.) and triethylamine (2 eq.) in N,N-dimethylformamide for 12 h at room temperature under Argon. The reaction mixture was then concentrated and purified by flash column chromatography to give 30.

Compound 30 (1 eq.) was reacted with linker 13 (3 eq.) in the presence of cuprous iodide (0.2 eq.), tetrakis(triphenylphosphine)palladium (0.2 eq.) and triethylamine (2 eq.) in N,N-dimethylformamide for 12 h at room temperature under Argon. The reaction is then concentrated and purified by flash column chromatography to give 31.

To a solution of 31 (0.3 mmoles) in anhydrous oxolane (10 mL) was added 1M tetrabutylammonium fluoride in oxolane (3 mL), and the mixture was stirred for 2 h at 0° C. After concentration the residue was purified by flash column chromatography providing 32.

3'-Fluoro-5-iodo-2',3'-dideoxycytidine 33 (1 eq.) was reacted with linker 32 (3 eq.) in the presence of cuprous iodide (0.2 eq.), tetrakis(triphenylphosphine)palladium (0.2 eq.) and triethylamine (2 eq.) in N,N-dimethylformamide for 12 h at room temperature under Argon. The reaction was concentrated purified by flash column chromatography to give 41.

Example 8

Figure 15:
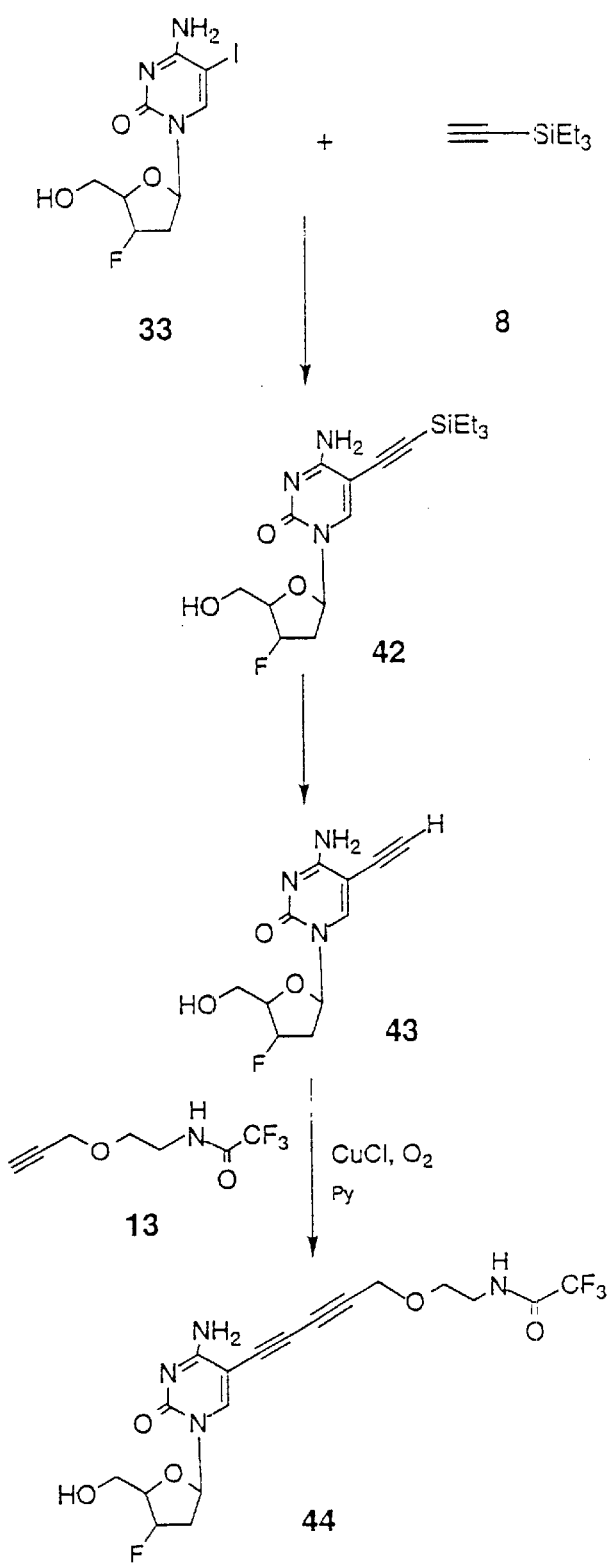
FIG. 15 shows the synthesis of compound 44 of the present invention.

Synthesis of Nucleoside-Protected-Linker Compound 44 (See FIG. 15)

3'-Fluoro-5-iodo-2',3'-dideoxycytidine 33 (1 eq.) was reacted with (triethylsilyl)acetylene 8 (4 eq.) in the presence of cuprous iodide (0.2 eq.), tetrakis(triphenylphosphine) palladium (0.2 eq.) and triethylamine (2 eq.) in N,N-dimethylformamide for 12 h at room temperature under Argon. The reaction was then concentrated and purified by flash column chromatography to give 42.

To a solution of 42 (1.86 mmoles) in anhydrous oxolane (10 mL) was added 1M tetrabutylammonium fluoride in oxolane (3 mL), and the mixture was stirred for 2 h at 0° C. After concentration it was purified by flash column chromatography providing 43.

Finally, a solution of nucleoside 43 (1 eq.) and linker 13 (8 eq.) in pyridine was stirred with CuCl (2 eq.), under $O_2$ at 35° C. for 2 h, diluted with ethyl acetate and successively washed with sat. aq. $NH_4Cl$ solution, brine, and water, dried, concentrated and purified by flash column chromatography to give 44.

Example 9

Figure 16:
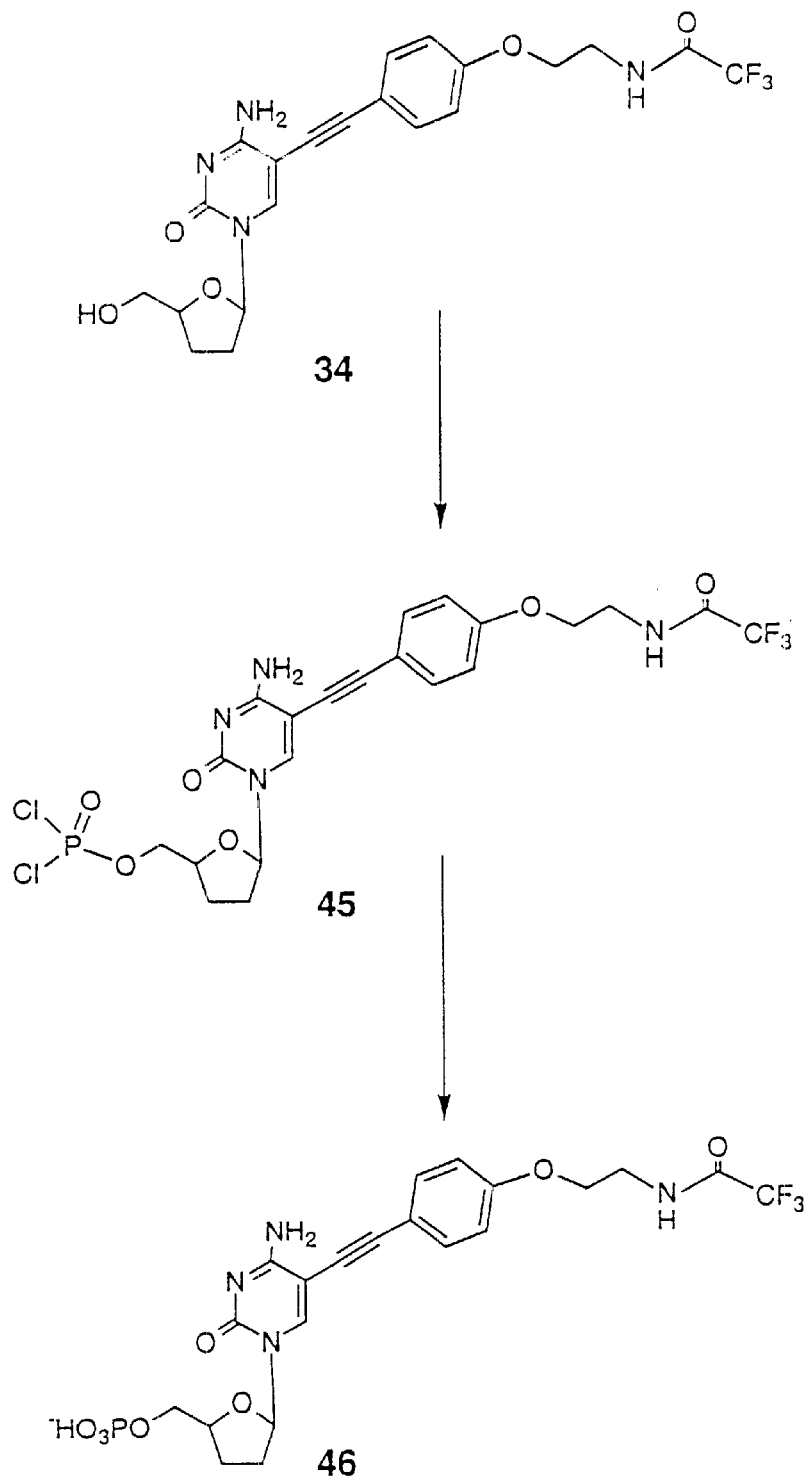
FIG. 16 shows the synthesis of compound 46 of the present invention.
Figure 17:
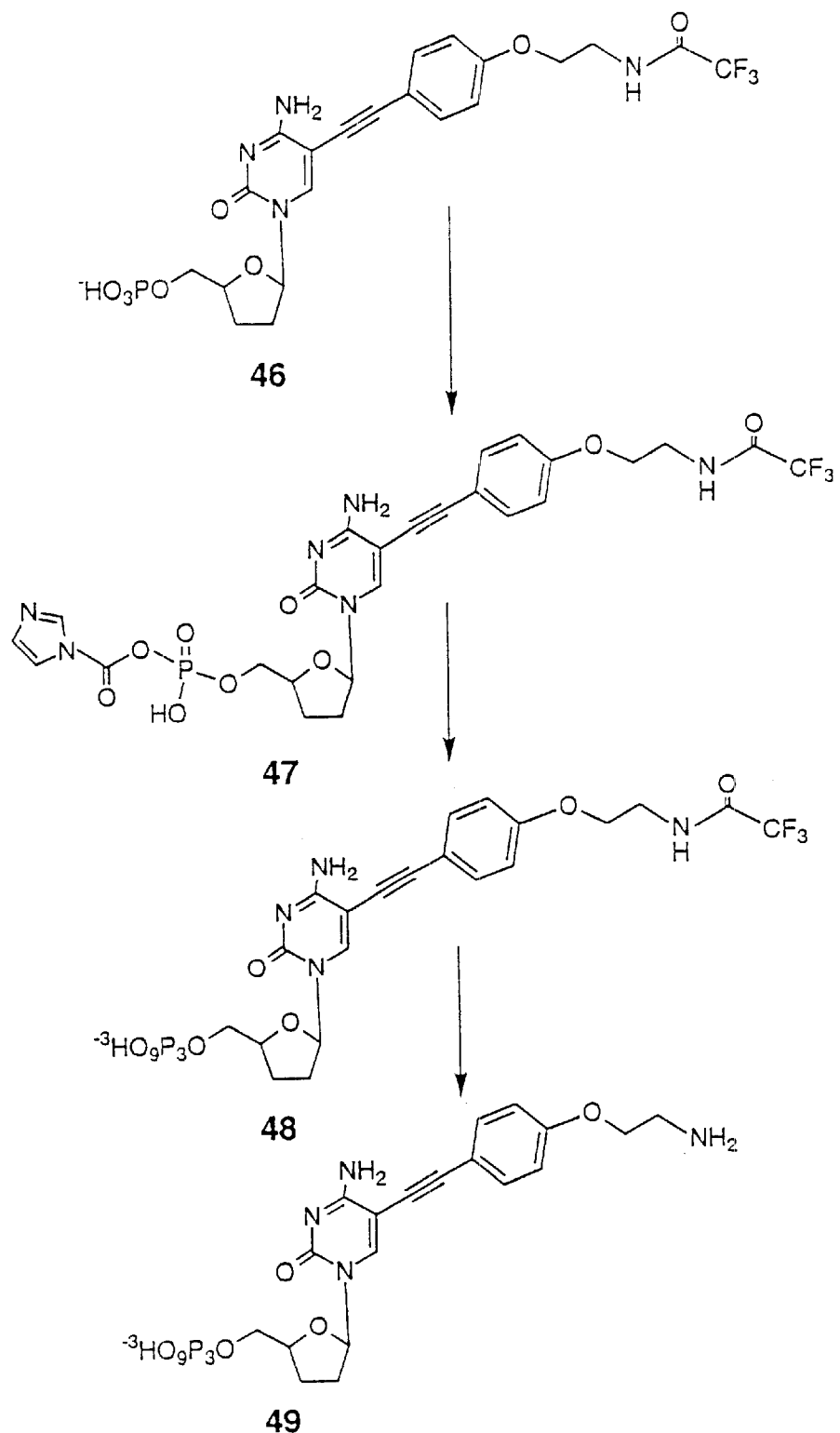
FIG. 17 shows the synthesis of compound 49 of the present invention.

Synthesis of Deprotected Nucleotide Triphosphate 49 (See FIGS. 16 and 17)

Freshly distilled phosphorous oxychloride (4 eq.) was added to nucleoside 34 (1 eq.) in trimethylphosphate at −30° C. to form the corresponding dichloromonophosphate 45. The reaction mixture was allowed to warm to 0° C. over a period of 60–90 minutes., the cooling bath was then removed and stirring was continued for 1–2 h at room temperature. The reaction was quenched with pH 8.0, 2 M TEAB buffer and purified by HPLC (C-18 reverse phase). The fractions corresponding to product were concentrated to give the monophosphate 46.

The monophosphate 46 (1 eq.) dissolved in N,N-dimethylformamide was stirred with So carbonyldiimidazole (CDI) (1.8 eq.) for 1 h at room temperature. Excess CDI was quenched with the addition of dry methanol. The activated monophosphate 47 was stirred with a solution of tributylammonium pyrophosphate (10 eq.) in N N-dimethylformamide containing n-tributylamine (5 eq.) for 12–24 h at room temperature. The reaction was quenched with 2 M TEAB pH 8.0 and purified by HPLC (C-18 reverse phase). The fractions corresponding to product were concentrated to give the protected nucleotide triphosphate 48.

The purified protected triphosphate 48 was taken up in concentrated aqueous $NH_4OH$ (2–5 mL) and stirred for 3 h at room temperature. The reaction mixture was concentrated to give 49 which was formulated with 0.1 M TEAB pH 7.0 to a concentration of 5–30 mM. The concentration and purity of the formulated bulk were confirmed by UV/Vis spectroscopy and C-18 reverse phase HPLC respectively.

Example 10

Figure 18:
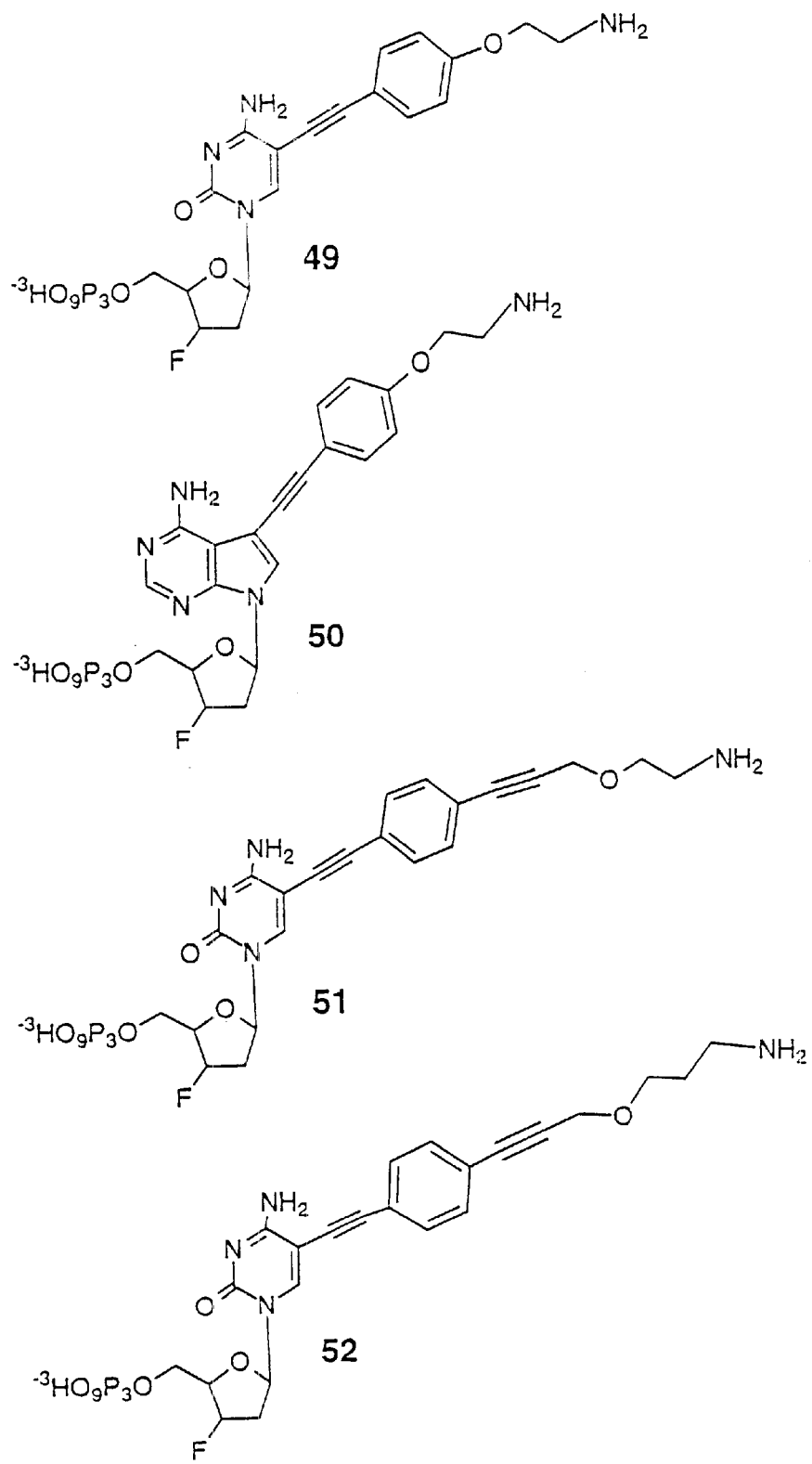
FIG. 18 shows the structures of compounds 49–52 of the present invention.
Figure 19:
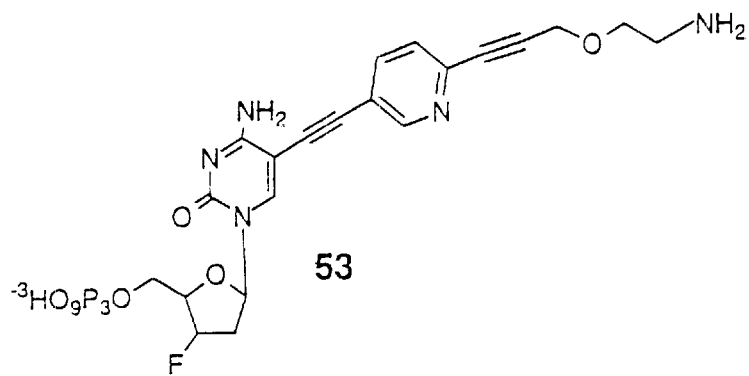
FIG. 19 shows the structures of compounds 53–56 of the present invention.
Figure 19:
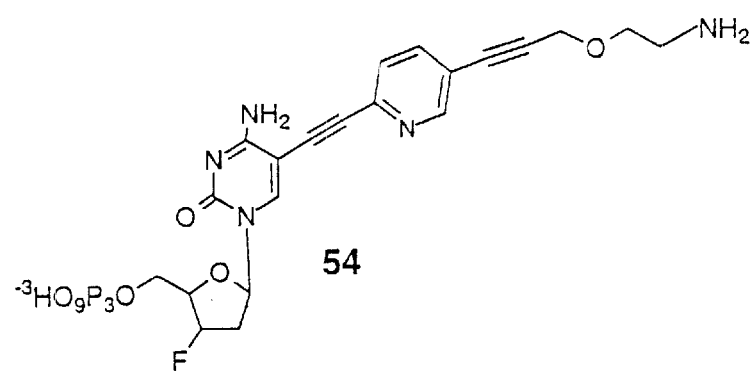
Figure 19:
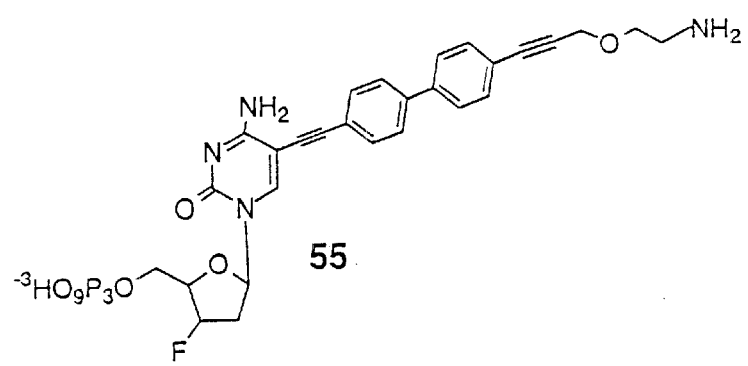
Figure 19:
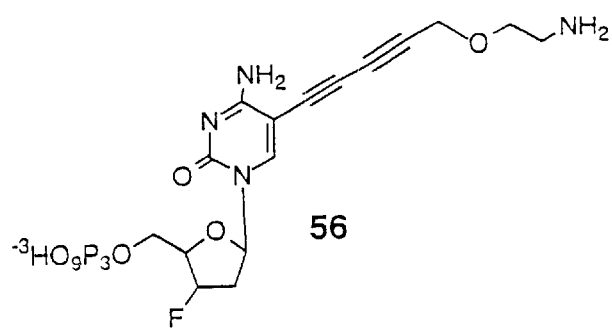

Conversion of Nucleoside-Protected-Linker Compounds to Deprotected Nucleotide Triphosphates (See FIGS. 18 and 19)

Nucleoside-protected-linker compounds 36, 37, 38, 39, 40, 41, and 44, (collectively "NPL" compounds) were converted to deprotected nucleotide triphosphate compounds 50, 51, 52, 53, 54, 55 and 56, as described in example 9 for the conversion of 34 to 49.

Example 11

Synthesis of Dye-Labeled Nucleotide Triphosphates

The deprotected nucleotide triphosphate compounds 49, 50, 51, 52, 53, 54, 55 and 56 from Example 9 and 10 were labeled with dye labels as follows. A deprotected nucleotide triphosphate compound in 100 mM TEA-bicarbonate (pH 7.0) was evaporated to dryness. It was then resuspended in 250 mM bicarbonate buffer (pH 9.0). A solution of Dye-NHS (in DMSO), (e.g., Jeb-NHS) was added and stirred in the dark at room temperature for 4–12 h. The reaction mixture was purified by HPLC (AX-300 anion exchange). The fractions corresponding to product were concentrated and repurified by HPLC (C-18 reverse phase). Final product was dried in vacuo and diluted with 250 mM CAPSO, pH 9.6, to a desired concentration. The concentration of the formulated bulk was confirmed by UV/VIS spectroscopy.

Example 12

Comparison of Peak-Height Evenness as a Function of Linkage Using the Terminator Titration Assay The Terminator Titration Assay was originally developed to determine the minimum amount of dye terminator required to create a full sequencing ladder, i.e., a sequencing ladder including all fragments terminating in a particular base having a length of between about 20 to about 600 nucleotides. The key components of the assay were (i) a primer labeled with a first dye, and (ii) a terminator labeled with a second dye spectrally resolvable from the first dye. In the assay, when an insufficient concentration of dye terminator was added to the sequencing reaction, no dideoxy-terminated fragments were formed, and all that was seen on the sequencing gel were products formed by "false stops" that were labeled with the first dye only. As used herein the term "false stops" refer to primer extension products not terminating in a dideoxy terminator, such products probably being formed when the polymerase enzyme spontaneously disengages from the template strand. When too much terminator was used, only short termination products were formed, i.e., less than about 50 nucleotides in length, such products including both the first and second dyes. When the proper amount of terminator was used, a fall sequencing ladder was produced, each fragment of the ladder being labeled with both the first and second dyes.

A modification of this assay was used to quantitatively compare the effect of changing the polymerase on different dye-terminators. The assay as described above was initially used to determine the minimum amount of dye terminator required for sequencing with AmpliTaq DNA Polymerase, FS. (The FS enzyme is a recombinant *Thermus aquaticus* DNA polymerase having two point mutations—G46D and F667Y). This concentration of dye terminator was then used with different mutated Thermus aquaticus DNA polymerases, where in addition to the 2 point mutations present in the FS mutant, additional point mutations have been introduced. Dye-labeled primers were not used.

The dye-terminator reactions were performed using AmpliTaq DNA Polymerase, FS or Thermus aquaticus DNA polymerase with additional point mutations following protocols provided in the ABI PRISM™ Dye Terminator Cycle Sequencing Core Kit Manual (PE Applied Biosystems p/n 402116). Reagents, including buffer, unlabeled primer, AmpliTaq DNA Polymerase, FS (when used), were from an ABI PRISM™ Dye Terminator Core Kit (PE Applied Biosystems p/n 402117). The dNTP mix consisted of 2 mM each of dATP, dCTP, dGTP, and dTTP. Pyrophosphatase (1 unit) was added to reactions with DNA polymerases other than FS, which is a commercial preparation which already includes the pyrophosphatase. The dye-terminators were those described in this application. A premix of reaction components was prepared as shown in the following table wherein all quantities are given on a per reaction basis.

| | |
|---|---|
| 5X Buffer | 4.0 µL |
| dNTP mix | 1.0 µL |
| Template: pGEM ® −3Zf(+), 0.2 µg/µL | 5.0 µL |
| Primer: −21 M13 (forward), 0.8 pmol/µL | 4.0 µL |
| AmpliTaq DNA Polymerase, FS | 0.5 µL |
| H$_2$O | 0.5 µL |

Reactions were assembled in 0.5 ml tubes adapted for the Perkin-Elmer 480 DNA Thermal Cycler (PE Applied Biosystems p/n N801-100). Reaction volumes were 20 µL, including 15 µL of the above reaction premix, a variable amount of dye labeled terminator, and a sufficient volume of water to bring the total reaction volume up to 20 µL. From 1 to 250 pmol of the dye terminator was added to each reaction. 30 µL of mineral oil was added to the top of each reaction to prevent evaporation. Reactions were thermocycled as follows: 96° C. for 30 sec, 50° C. for 15 sec, and 60° C. for 4 min, for 25 cycles; followed by a 4° C. hold cycle.

All reactions were purified by spin-column purification on Centri-Sep spin columns according to manufacturer's instructions (Princeton Separations p/n CS-901). Gel material in the column was hydrated with 0.8 mL deionized water for at least 30 minutes at room temperature. After the column was hydrated and it was determined that no bubbles were trapped in the gel material, the upper and lower end caps of the column were removed, and the column was allowed to drain by gravity. The column was then inserted into the wash tubes provided in the kit and centrifuged in a variable speed microcentrifuge at 1300× g for 2 minutes, removed from the wash tube, and inserted into a sample collection tube. The reaction mixture was carefully removed from under the oil and loaded onto the gel material. Columns were centrifuged in a variable speed microcentrifuge at 1300× g for 2 minutes. Eluted samples were then dried in a vacuum centrifuge.

Prior to loading onto a sequencing gel, the dried samples were resuspended in 25 AL of Template Suppression Reagent (PE Applied Biosystems p/n 401674), vortexed, heated to 95° C. for 2 minutes, cooled on ice, vortexed again, and centrifuged (13,000× g). 10 µL of the resuspended sample was aliquoted into sample vials (PE Applied Biosystems p/n 401957) adapted for the PE ABI PRISM™ 310 Genetic Analyzer (PE Applied Biosystems p/n 310 00-100/120). Electrophoresis on the 310 Genetic Analyzer was performed with sieving polymers and capillaries specially adapted for DNA sequencing analysis (PE Applied Biosystems p/n 402837 (polymer) and p/n 402840 (capillary)). In each case, the sieving polymer included nucleic acid denaturants. Samples were electrokinetically injected onto the capillary for 30 sec at 2.5 kV, and run for 2 hr at 10 to 12.2 kV with the outside wall of the capillary maintained at 50° C.

The C peaks present in the first 220 bases of the pGEM sequence were evaluated by a computer program, Stat Tool, to determine the mean peak height and the standard deviation of the mean peak height. The relative error was calculated as the ratio of the standard deviation of mean peak height divided by the mean peak height. This value is a measure of the relative evenness of the peaks. The more even the peaks the lower the relative error.

Table 1 shows the results of an experiment comparing the peak evenness of sequencing reactions in which three terminators with three different linkages were used; two conventional linkages and one linkage according to the present invention. The structures of the three linkages are as follows:

propargylamino (AP),

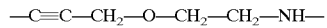

propargyl-ethyl-oxide-amino (EO),

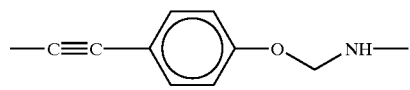

acetylene-phenyl-ethyl-oxide-amino (PH-EO, 49).

The terminator (ddCTP) and dye (HEX-1) were the same in these experiments. In addition, we used AmpliTaq FS and a mutant polymerase which further included a R660S mutation. These data show that for the best peak evenness with these rigid linkers it is preferable to use a mutant enzyme, and, that the combination of the mutant enzyme and the rigid linker results in better peak evenness than can otherwise be achieved (AmpliTaq FS with EO linker: 0.342 vs R660S with PH-EO linker 0.224).

TABLE 1

| Dye Terminator | ddC-AP-HEX-1 | ddC-EO-HEX-1 | dC-Ph-EO-HEX-1 |
|---|---|---|---|
| FS | 0.788 | 0.342 | 0.814 |
| FS-R660S | 0.596 | 0.387 | 0.295 |
| FS-R660S + ppase | 0.689 | 0.374 | 0.224 |

All publications and patent applications are herein incorporated by reference to the same extent as if each individual publication or patent application was specifically and individually indicated to be incorporated by reference.

Although only a few embodiments have been described in detail above, those having ordinary skill in the chemical and molecular biology arts will clearly understand that many modifications are possible in the preferred embodiment without departing from the teachings thereof. All such modifications are intended to be encompassed within the following claims.

We claim:

1. A nucleoside/tide compound comprising the structure:

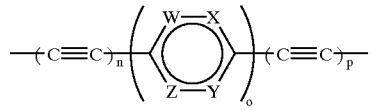

wherein:
  NUC is a nucleoside/tide having a nucleobase B;
  L is a rigid linkage having the structure:
  wherein
    each of n, o and p are integers ranging from 0 to 3, and the sum of n, o and p is at least 2; and
    each of W, X, Y and Z is independently selected from CH and N, including substituted forms thereof;
  S is a spacer selected from $C_1$–$C_8$ lower alkyl, lower alkylene oxide, amide, carbamate, and sulfonamide;

wherein lower alkylene oxide is selected from the structures:

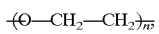

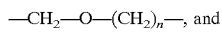, and

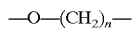

where n is an integer from 1 to 8; and

LB/LG is an amino group, a protected amino or a label, wherein label is selected from a rhodamine-type dye and a fluorescein-type dye;

wherein NUC is attached to L through the nucleobase B such that when B is a purine, L is attached to the 8-position of the purine, when B is 7-deazapurine, L is attached to the 7-position of the 7-deazapurine, and when B is pyrimidine, L is attached to the 5-position of the pyrimidine.

2. The compound of claim 1 wherein NUC is selected from 2'-deoxyribonucleotide, 3'-deoxyribonucleotide, 2',3'-dideoxyribonucleotide, 2',3'-dideoxy-3'-fluoro-ribonucleotide, 2',3'-dideoxy-2'-fluoro-ribonucleotide, 2',3'-dideoxy-3'-azido-ribonucleotide, 2',3'-dideoxy-2'-azido-ribonucleotide, 2',3'-dideoxy-2'-amino-ribonucleotide, 2',3'-dideoxy-3'-amino-ribonucleotide, 2',3'-dehydroribonucleotide and ribonucleotide.

3. The compound of claim 1 wherein NUC is 2'-deoxyribonucleotide.

4. The compound of claim 1 wherein B is selected from adenine, guanine, cytosine, uracil, thymine, deazaadenine, and deazaguanosine.

5. The compound of claim 1 wherein B is selected from 2,6-diaminopurine, hypoxanthine, pseudouridine, C-5-propyne, isocytosine, isoguanine, and 2-thiopyrimidine.

6. The compound of claim 1 wherein NUC is selected from 2',3'-dideoxy-3'-fluoro-ribonucleotide.

7. The compound of claim 1 wherein NUC is a 5' hydroxyl nucleoside.

8. The compound of claim 1 wherein NUC is a 5' triphosphate nucleotide.

9. The compound of claim 1 wherein n is 1 or 2.

10. The compound of claim 1 wherein o is 1 or 2.

11. The compound of claim 1 wherein p is 0 or 1.

12. The compound of claim 1 wherein n is 1 or 2, o is 1 or 2, and p is 0 or 1.

13. The compound of claim 1 wherein S has the structure:

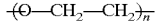

where n is an integer from 1 to 8.

14. The compound of claim 13 wherein n is 1 and LB/LG is $NH_2$.

15. The compound of claim 13 wherein n is 1 and LB/LG is $NHC(O)CF_3$.

16. The compound of claim 13 wherein n is 1 and LB/LG is a fluorescein-type dye.

17. The compound of claim 13 wherein n is 1 and LB/LG is a rhodamine-type dye.

18. The compound of claim 1 wherein S has the structure:

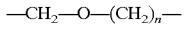

where n is an integer from 1 to 8.

19. The compound of claim 18 wherein n is 2 and LB/LG is $NH_2$.

20. The compound of claim 18 wherein n is 2 and LB/LG is $NHC(O)CF_3$.

21. The compound of claim 18 wherein n is 2 and LB/LG is a fluorescein-type dye.

22. The compound of claim 18 wherein n is 2 and LB/LG is a rhodamine-type dye.

23. The compound of claim 18 wherein n is 3 and LB/LG is $NH_2$.

24. The compound of claim 18 wherein n is 3 and LB/LG is $NHC(O)CF_3$.

25. The compound of claim 18 wherein n is 3 and LB/LG is a fluorescein-type dye.

26. The compound of claim 18 wherein n is 3 and LB/LG is a rhodamine-type dye.

27. The compound of claim 1 wherein S has the structure:

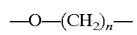

where n is an integer from 1 to 8.

28. The compound of claim 27 wherein n is 2 and LB/LG is $NH_2$.

29. The compound of claim 27 wherein n is 2 and LB/LG is $NHC(O)CF_3$.

30. The compound of claim 27 wherein n is 2 and LB/LG is a fluorescein-type dye.

31. The compound of claim 27 wherein n is 2 and LB/LG is a rhodamine-type dye.

32. The compound of claim 1 wherein L has the structure:

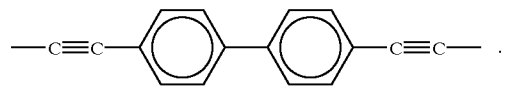

33. The compound of claim 1 wherein L has the structure:

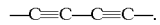

34. The compound of claim 1 wherein L has the structure:

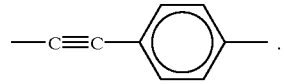

35. The compound of claim 1 wherein L has the structure:

36. The compound of claim 1 wherein L has the structure:

37. The compound of claim 1 wherein L has the structure:

* * * * *

UNITED STATES PATENT AND TRADEMARK OFFICE
CERTIFICATE OF CORRECTION

PATENT NO. : 6,653,462 B2  Page 1 of 1
APPLICATION NO. : 10/085561
DATED : November 25, 2003
INVENTOR(S) : Khan et al.

It is certified that error appears in the above-identified patent and that said Letters Patent is hereby corrected as shown below:

Column 20, lines 50 through 60,
Please remove:
"1. A nucleoside/tide compound comprising the structure:

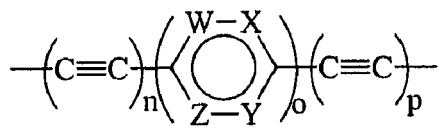

wherein:
 NUC is a nucleoside/tide having a nucleobase B;
 L is a rigid linkage having the structure:"

and replace with:
--1. A nucleoside/tide compound comprising the structure

wherein:
 NUC is a nucleoside/tide having a nucleobase B;
 L is a rigid linkage having the structure:

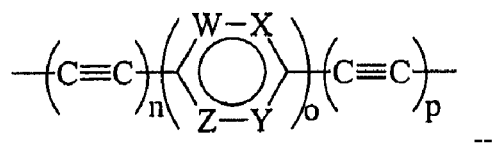

--

Signed and Sealed this

Nineteenth Day of February, 2008

JON W. DUDAS
*Director of the United States Patent and Trademark Office*